(12) United States Patent
Shamanin et al.

(10) Patent No.: US 6,395,512 B1
(45) Date of Patent: *May 28, 2002

(54) DNA CODING FOR A PEPTIDE OF A PAPILLOMA VIRUS MAIN CAPSIDE PROTEIN AND USE THEREOF

(75) Inventors: Vladimir Shamanin, Heidelberg; Ethel-Michele De Villiers-Zur Hausen, Hirschberg, both of (DE); Irene Leigh, London (GB); Harald Zur Hausen, Hirschberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/430,010

(22) Filed: Oct. 29, 1999

Related U.S. Application Data

(63) Continuation of application No. 08/578,634, filed as application No. PCT/EP95/01697 on May 4, 1995, now Pat. No. 6,025,163.

(30) Foreign Application Priority Data

May 4, 1994 (DE) .......................................... 44 157 43

(51) Int. Cl.[7] .......................... C12P 21/06; C12N 15/00
(52) U.S. Cl. .................. 435/69.3; 435/69.1; 435/252.3; 435/320.1; 530/350; 530/403; 536/23.72
(58) Field of Search ............................. 435/69.3, 69.1, 435/252.3, 320.1; 530/350, 403; 536/23.72

(56) References Cited

FOREIGN PATENT DOCUMENTS

| WO | WO A91 18294 | 2/1991 |
|---|---|---|
| WO | WO A93 02184 | 5/1993 |
| WO | WO A94 00152 | 1/1994 |
| WO | WO A94 05792 | 3/1994 |
| WO | WO A94 20137 | 9/1994 |

OTHER PUBLICATIONS

Volpers et al. Virology, vol. 181, pp. 419–423, 1991.*

Shamanin, et al., Sep. 1994, "Specific types of human papillomavirus found in benign proliferations and carcinomas of the skin in immunosuppressed patients", *Cancer Research* 17:4610–4613.

zur Hausen, 1989, *Cancer Research* 49:4677–4681.

zur Hausen, 1976, *Cancer Research* 36:530.

Syrjänen, 1980, *Lung 158*:131–142.

Kirnbaur, et al., 1993, *J. Virology* 6929–6936.

Hagensee, et al., 1993, *J. Virology* 315–322.

Rose et al., 1993, J. of Virology, vol. 67(4), pp. 1936–1944.

Tomita et al., 1987, J. of Virology, vol. 61(8), pp. 2389–2394.

Tomita et al., 1987, J. of Virology, vol. 158, pp. 8–14.

* cited by examiner

Primary Examiner—Ali R. Salimi
(74) *Attorney, Agent, or Firm*—Pennie & Edmonds LLP

(57) ABSTRACT

This invention relates to a DNA encoding a peptide of a papilloma virus major capsid protein. Furthermore, this invention deals with a papilloma virus genome containing such a DNA. In addition, this invention concerns proteins encoded by the papilloma virus genome and virus-like particles as well as antibodies directed thereagainst and the use thereof and the use thereof in diagnosis, treatment and vaccination.

16 Claims, 19 Drawing Sheets

FIG. 1-A

```
    GGTAGAGGACAGCCATTAGGCGTGGGGTTAAGTGGACACCCTCTGTATAACAAACTGAAT
  1 ----------+----------+----------+----------+----------+----------+  60
    CCATCTCCTGTCGGTAATCCGCACCCCAATTCACCTGTGGGAGACATATTGTTTGACTTA a    G  R  G  Q  P  L  G  V  G  L  S  G  H  P  L  Y  N  K  L  N    -

GACACTGAAAACTCCAACATTGCACATGCTGACAATAGTCCTGACTCCCGGGACAACATT
 61 ----------+----------+----------+----------+----------+----------+ 120
    CTGTGACTTTTGAGGTTGTAACGTGTACGACTGTTATCAGGACTGAGGGCCCTGTTGTAA a    D  T  E  N  S  N  I  A  H  A  D  N  S  P  D  S  R  D  N  I    -

TCTGTTGACTGTAAGCAAACACAACTGTGCATACTGGGCTGTACGCCCCCCATGGGGGAA
121 ----------+----------+----------+----------+----------+----------+ 180
    AGACAACTGACATTCGTTTGTGTTGACACGTATGACCCGACATGCGGGGGGTACCCCCTT a    S  V  D  C  K  Q  T  Q  L  C  I  L  G  C  T  P  P  M  G  E    -

TACTGGGGTAAGGGTACCCCTTGTGCACGTACTAATACTACCCCAGGAGACTGTCCTCCC
181 ----------+----------+----------+----------+----------+----------+ 240
    ATGACCCCATTCCCATGGGGAACACGTGCATGATTATGATGGGGTCCTCTGACAGGAGGG a    Y  W  G  K  G  T  P  C  A  R  T  N  T  T  P  G  D  C  P  P    -

TTGGAGTTAATGACATCTTATATTCAGGATGGCGACATGGTGGATACCGGGTATGGTGCC
241 ----------+----------+----------+----------+----------+----------+ 300
    AACCTCAATTACTGTAGAATATAAGTCCTACCGCTGTACCACCTATGGCCCATACCACGG a    L  E  L  M  T  S  Y  I  Q  D  G  D  M  V  D  T  G  Y  G  A    -

ATGGACTTTACTGCCCTGCAATTTAATAAGTCTGACGTGCCCCTTGATATTTGCCAGTCT
301 ----------+----------+----------+----------+----------+----------+ 360
    TACCTGAAATGACGGGACGTTAAATTATTCAGACTGCACGGGGAACTATAAACGGTCAGA a    M  D  F  T  A  L  Q  F  N  K  S  D  V  P  L  D  I  C  Q  S    -

ATTTGCAAATATCCCGATTATTTGGGCATGGCTGCCGACCCGTATGGCGATAGCATGTTC
361 ----------+----------+----------+----------+----------+----------+ 420
    TAAACGTTTATAGGGCTAATAAACCCGTACCGACGGCTGGGCATACCGCTATCGTACAAG a    I  C  K  Y  P  D  Y  L  G  M  A  A  D  P  Y  G  D  S  M  F    -

TTTTTCCTCCGTCGGGAACAACTGTTTGCCAGACACTTTTTCAATCGTGCGGGTGATGTT
421 ----------+----------+----------+----------+----------+----------+ 480
    AAAAAGGAGGCAGCCCTTGTTGACAAACGGTCTGTGAAAAAGTTAGCACGCCCACTACAA a    F  F  L  R  R  E  Q  L  F  A  R  H  F  F  N  R  A  G  D  V    -
```

FIG. 1-B

```
        GGAGACAAAATTCCAGAATCTTTGTACCTCAAAGGGAGTAGCGGGCGTGAGACTCCCGGC
    481 ---------+---------+---------+---------+---------+---------+ 540
        CCTCTGTTTTAAGGTCTTAGAAACATGGAGTTTCCCTCATCGCCCGCACTCTGAGGGCCG a        G  D  K  I  P  E  S  L  Y  L  K  G  S  S  G  R  E  T  P  G   -

AGTGCTATATACAGCCCCACACCCAGTGGGTCTATGGTGACCTCTGAGGCACAAATATTC
    541 ---------+---------+---------+---------+---------+---------+ 600
        TCACGATATATGTCGGGGTGTGGGTCACCCAGATACCACTGGAGACTCCGTGTTTATAAG a        S  A  I  Y  S  P  T  P  S  G  S  M  V  T  S  E  A  Q  I  F   -

AATAAGTCTTACTGGCTACAGCAAGCTCAAGGCCAAAATAACGGTAT
    601 ---------+---------+---------+---------+------- 647
        TTATTCAGAATGACCGATGTCGTTCGAGTTCCGGTTTTATTGCCATA a        N  K  S  Y  W  L  Q  Q  A  Q  G  Q  N  N  G      -
```

FIG. 2-A

```
    TCAAGAGGACACCCATTAGGAGTAGGGTCTACAGGTCATCCCCTATTTAATAAAGTGAAG
  1 ------------+----------+----------+----------+----------+----------+  60
    AGTTCTCCTGTGCGTAATCCTCATCCCAGATGTCCAGTAGGGGATAAATTATTTCACTTC
```
a     S R G H P L G V G S T G H P L F N K V K

```
    GATACGGAAAATGCTAATAATTATATAGTAACATCTAAGGATGATAGGCAGGACACCTCA
 61 ------------+----------+----------+----------+----------+----------+ 120
    CTATGCCTTTTACGATTATTAATATATCATTGTAGATTCCTACTATCCGTCCTGTGGAGT
```
a     D T E N A N N Y I V T S K D D R Q D T S

```
    TTTGATCCTAAACAGGTTCAAATGTTTATTATTGGCTGCGCACCGTGCATAGGTGAGCAC
121 ------------+----------+----------+----------+----------+----------+ 180
    AAACTAGGATTTGTCCAAGTTTACAAATAATAACCGACGCGTGGCACGTATCCACTCGTG
```
a     F D P K Q V Q M F I I G C A P C I G E H

```
    TGGGATGCAGCCAAGCCCTGTGATGCTGACAGAGGGGTAGGCAAATGTCCACCTTTGGAA
181 ------------+----------+----------+----------+----------+----------+ 240
    ACCCTACGTCGGTTCGGGACACTACGACTGTCTCCCCATCCGTTTACAGGTGGAAACCTT
```
a     W D A A K P C D A D R G V G K C P P L E

```
    CTGGTAAATACTGTAATAGAAGATGGAGATATGGTGGATATAGGTTTTGGAAATATAAAT
241 ------------+----------+----------+----------+----------+----------+ 300
    GACCATTTATGACATTATCTTCTACCTCTATACCACCTATATCCAAAACCTTTATATTTA
```
a     L V N T V I E D G D M V D I G F G N I N

```
    AATAAAACCCTGTCAGCAAATAAGTCAGATGTCAGTTTAGATATAGTTAATAATATTTGT
301 ------------+----------+----------+----------+----------+----------+ 360
    TTATTTTGGGACAGTCGTTTATTCAGTCTACAGTCAAATCTATATCAATTATTATAAACA
```
a     N K T L S A N K S D V S L D I V N N I C

```
    AAGTATCCAGACTTTTTAAAAATGGCCAATGACATATATGGAGACTCCTGTTTTTTTTAT
361 ------------+----------+----------+----------+----------+----------+ 420
    TTCATAGGTCTGAAAAATTTTTACCGGTTACTGTATATACCTCTGAGGACAAAAAAAATA
```
a     K Y P D F L K M A N D I Y G D S C F F Y

```
    GCTAGACGGGAGCAATGTTATGCTAGACATTTTTTTGTTAGAGGAGGTAATGTAGGAGAT
421 ------------+----------+----------+----------+----------+----------+ 480
    CGATCTGCCCTCGTTACAATACGATCTGTAAAAAAACAATCTCCTCCATTACATCCTCTA
```
a     A R R E Q C Y A R H F F V R G G N V G D

FIG. 2-B

```
        GCTATTCCTGATGCTGCAGTGGGTCAGGACAATAACTTTGTGTTGCCTGCAGCTGTTGGA
    481 ----------+----------+----------+----------+----------+----------+ 540
        CGATAAGGACTACGACGTCACCCAGTCCTGTTATTGAAACACAACGGACGTCGACAACCT a        A  I  P  D  A  A  V  G  Q  D  N  N  F  V  L  P  A  A  V  G   -

CAGGCCCAAAACACTTTGGGTAGCTCTATTTACGTGCCTACCGTTAGTGGTTCTTTGGTA
    541 ----------+----------+----------+----------+----------+----------+ 600
        GTCCGGGTTTTGTGAAACCCATCGAGATAAATGCACGGATGGCAATCACCAAGAAACCAT a        Q  A  Q  N  T  L  G  S  S  I  Y  V  P  T  V  S  G  S  L  V   -

TCCACAGATGCACAATTATTTAATAGGCCCTTTTGGCTACAACGAGCACAGGGTCATAAT
    601 ----------+----------+----------+----------+----------+----------+ 660
        AGGTGTCTACGTGTTAATAAATTATCCGGGAAAACCGATGTTGCTCGTGTCCCAGTATTA a        S  T  D  A  Q  L  F  N  R  P  F  W  L  Q  R  A  Q  G  H  N   -

AACGGTAT
    661 -------- 668
        TTGCCATA
```

FIG. 3-A

```
    TCTAGGGGGCAACCCTTGGGGGTAGGTTCTACAGGCCATCCTTTGTTCAATAAAGTAAAG
  1 ------------+----------+----------+----------+----------+----------+  60
    AGATCCCCCGTTGGGAACCCCCATCCAAGATGTCCGGTAGGAAACAAGTTATTTCATTTC a     S  R  G  Q  P  L  G  V  G  S  T  G  H  P  L  F  N  K  V  K   -

GATACTGAAAATTCAAATAATTATATAACAATGTCTAAAGATGATAGGCAGGACACCTCG
 61 ------------+----------+----------+----------+----------+----------+ 120
    CTATGACTTTTAAGTTTATTAATATATTGTTACAGATTTCTACTATCCGTCCTGTGGAGC a     D  T  E  N  S  N  N  Y  I  T  M  S  K  D  D  R  Q  D  T  S   -

TTTGACCCTAAGCAGGTTCAAATGTTTATTATTGGCTGTGCACCTTGTATAGGGGAGCAC
121 ------------+----------+----------+----------+----------+----------+ 180
    AAACTGGGATTCGTCCAAGTTTACAAATAATAACCGACACGTGGAACATATCCCCTCGTG a     F  D  P  K  Q  V  Q  M  F  I  I  G  C  A  P  C  I  G  E  H   -

TGGGATGCTGCCAAACCCTGTGACGCTGACAAAGGAGACGGTAAATGTCCACCTTTAGAA
181 ------------+----------+----------+----------+----------+----------+ 240
    ACCCTACGACGGTTTGGGACACTGCGACTGTTTCCTCTGCCATTTACAGGTGGAAATCTT a     W  D  A  A  K  P  C  D  A  D  K  G  D  G  K  C  P  P  L  E   -

TTAGTAAATACAGTTATTGAGGATGGGGATATGGTGGATATAGGTTTTGGTAACATAAAT
241 ------------+----------+----------+----------+----------+----------+ 300
    AATCATTTATGTCAATAACTCCTACCCCTATACCACCTATATCCAAAACCATTGTATTTA a     L  V  N  T  V  I  E  D  G  D  M  V  D  I  G  F  G  N  I  N   -

AATAAAACCTTGTCAGCAAATAAATCAGATGTCAGTTTGGATATAGTTAATAACATTTGT
301 ------------+----------+----------+----------+----------+----------+ 360
    TTATTTTGGAACAGTCGTTTATTTAGTCTACAGTCAAACCTATATCAATTATTGTAAACA a     N  K  T  L  S  A  N  K  S  D  V  S  L  D  I  V  N  N  I  C   -

AAGTATCCAGACTTCCTTAAAATGGCCAATGACATATATGGGGACTCCTGTTTTTTTTAT
361 ------------+----------+----------+----------+----------+----------+ 420
    TTCATAGGTCTGAAGGAATTTTACCGGTTACTGTATATACCCCTGAGGACAAAAAAAATA a     K  Y  P  D  F  L  K  M  A  N  D  I  Y  G  D  S  C  F  F  Y   -

GCCAGGCGGGAACAATGTTATGCTAGACACTTTTTTGTTAGGGGAGGCAATGTAGGCGAT
421 ------------+----------+----------+----------+----------+----------+ 480
    CGGTCCGCCCTTGTTACAATACGATCTGTGAAAAAACAATCCCCTCCGTTACATCCGCTA a     A  R  R  E  Q  C  Y  A  R  H  F  F  V  R  G  G  N  V  G  D   -
```

FIG. 3-B

```
         CGAATTCCTAATGCTGCAGTGGGTCAGGACAATAATTTTATGTTACCTGCAGCCGCTGGG
     481 ----------+----------+----------+----------+----------+----------+ 540
         GCTTAAGGATTACGACGTCACCCAGTCCTGTTATTAAAATACAATGGACGTCGGCGACCC a        R  I  P  N  A  A  V  G  Q  D  N  N  F  M  L  P  A  A  A  G      -

CAGGCTCAAAACACTTTGGGCAACTCTATTTATGTTCCCACGGTCAGTGGTTCTTTGGTG
     541 ----------+----------+----------+----------+----------+----------+ 600
         GTCCGAGTTTTGTGAAACCCGTTGAGATAAATACAAGGGTGCCAGTCACCAAGAAACCAC a        Q  A  Q  N  T  L  G  N  S  I  Y  V  P  T  V  S  G  S  L  V      -

TCCACAGATGCTCAATTATTTAACAGGCCATTTTGGCTGCAACGAGCACAAGGTCACAAC
     601 ----------+----------+----------+----------+----------+----------+ 660
         AGGTGTCTACGAGTTAATAAATTGTCCGGTAAAACCGACGTTGCTCGTGTTCCAGTGTTG a        S  T  D  A  Q  L  F  N  R  P  F  W  L  Q  R  A  Q  G  H  N      -

```
        GGAAGTGGTCTTCCATTAGGCATAGGCAGCAGTGGTCACCCTCTGTTTAACAAGGTAAAT
     1  ------------+----------+----------+----------+----------+----------+   60
        CCTTCACCAGAAGGTAATCCGTATCCGTCGTCACCAGTGGGAGACAAATTGTTCCATTTA a         G  S  G  L  P  L  G  I  G  S  S  G  H  P  L  F  N  K  V  N    -

GATACAGAAAATGGCAACACATATAAAGGGACAACTAAAGATGATAGACAAAACATTTCA
    61  ------------+----------+----------+----------+----------+----------+  120
        CTATGTCTTTTACCGTTGTGTATATTTCCCTGTTGATTTCTACTATCTGTTTTGTAAAGT a         D  T  E  N  G  N  T  Y  K  G  T  T  K  D  D  R  Q  N  I  S    -

TTTGATCCTAAACAATTACAGATGTTTATAATTGGCTGTACACCATGTATTGGTGAACAT
   121  ------------+----------+----------+----------+----------+----------+  180
        AAACTAGGATTTGTTAATGTCTACAAATATTAACCGACATGTGGTACATAACCACTTGTA a         F  D  P  K  Q  L  Q  M  F  I  I  G  C  T  P  C  I  G  E  H    -

TGGGATAAGGCTCCTGCATGTGTTAATGATATTCAACAAGGTAGTTGCCCACCAATAGAA
   181  ------------+----------+----------+----------+----------+----------+  240
        ACCCTATTCCGAGGACGTACACAATTACTATAAGTTGTTCCATCAACGGGTGGTTATCTT a         W  D  K  A  P  A  C  V  N  D  I  Q  Q  G  S  C  P  P  I  E    -

TTAGTTAACACATACATACAGGGTGGAGATATGGCTGATATAGGATATGGCAATCTAAAT
   241  ------------+----------+----------+----------+----------+----------+  300
        AATCAATTGTGTATGTATGTCCCACCTCTATACCGACTATATCCTATACCGTTAGATTTA a         L  V  N  T  Y  I  Q  G  G  D  M  A  D  I  G  Y  G  N  L  N    -

TTTAAAGCTTTACAGCAAAATAGATCAGATGTTAGCTTGGATATTGTAGATGAAATATGC
   301  ------------+----------+----------+----------+----------+----------+  360
        AAATTTCGAAATGTCGTTTTATCTAGTCTACAATCGAACCTATAACATCTACTTTATACG a         F  K  A  L  Q  Q  N  R  S  D  V  S  L  D  I  V  D  E  I  C    -

AAATATCCTGACTTTTTACGAATGCAAAATGATGTATATGGCGATGCCTGTTTTTTTTAT
   361  ------------+----------+----------+----------+----------+----------+  420
        TTTATAGGACTGAAAAATGCTTACGTTTTACTACATATACCGCTACGGACAAAAAAAATA a         K  Y  P  D  F  L  R  M  Q  N  D  V  Y  G  D  A  C  F  F  Y    -

GCTCGACGGGAGCAATGTTATGCCAGGCACTTTTTTGTGCGTGGTGGCAAACCTGGTGAT
   421  ------------+----------+----------+----------+----------+----------+  480
        CGAGCTGCCCTCGTTACAATACGGTCCGTGAAAAAACACGCACCACCGTTTGGACCACTA a         A  R  R  E  Q  C  Y  A  R  H  F  F  V  R  G  G  K  P  G  D    -
```

FIG. 4-B

```
        GATATACCTGGTGCCCAAATTGATGCAGGGTCACATAAAAATGAATATTACATACAGGCA
    481 ----------+----------+----------+----------+---------+---------+ 540
        CTATATGGACCACGGGTTTAACTACGTCCCAGTGTATTTTTACTTATAATGTATGTCCGT a        D  I  P  G  A  Q  I  D  A  G  S  H  K  N  E  Y  Y  I  Q  A   -

GCTTCAGACCAATCACAAAATAGTTTGGGGAATTCTATGTATTTCCCAACTATCAGTGGC
    541 ----------+----------+----------+----------+---------+---------+ 600
        CGAAGTCTGGTTAGTGTTTTATCAAACCCCTTAAGATACATAAAGGGTTGATAGTCACCG a        A  S  D  Q  S  Q  N  S  L  G  N  S  M  Y  F  P  T  I  S  G   -

TCATTAGTTTCAAGTGATGCTCAATTATTTAATAGGCCCTTCTGGCTACAGCGAGCACAA
    601 ----------+----------+----------+----------+---------+---------+ 660
        AGTAATCAAAGTTCACTACGAGTTAATAAATTATCCGGGAAGACCGATGTCGCTCGTGTT a        S  L  V  S  S  D  A  Q  L  F  N  R  P  F  W  L  Q  R  A  Q   -

GGCCAAAACAACGGGAT
    661 ----------+------- 677
        CCGGTTTTGTTGCCCTA
```

FIG. 5-A

```
    TCAAGGGGACAGCCATTGGGTGTAGGAACATCAGGTCATCCTTTATTTAACAAAGTCAGG
  1 ----------+----------+----------+----------+----------+----------+ 60
    AGTTCCCCTGTCGGTAACCCACATCCTTGTAGTCCAGTAGGAAATAAATTGTTTCAGTCC
``` a      S   R   G   Q   P   L   G   V   G   T   S   G   H   P   L   F   N   K   V   R     -

```
    GATACTGAAAACTCAGGTAACTATCAAGCAGTTTCTCAGGATGACAGACAAAATACATCT
 61 ----------+----------+----------+----------+----------+----------+ 120
    CTATGACTTTTGAGTCCATTGATAGTTCGTCAAAGAGTCCTACTGTCTGTTTTATGTAGA
``` a      D   T   E   N   S   G   N   Y   Q   A   V   S   Q   D   D   R   Q   N   T   S     -

```
    TTTGATCCTAAACAAGTGCAAATGTTTGTCATTGGCTGTGTGCCGTGTATGGGTGAACAT
121 ----------+----------+----------+----------+----------+----------+ 180
    AAACTAGGATTTGTTCACGTTTACAAACAGTAACCGACACACGGCACATACCCACTTGTA
``` a      F   D   P   K   Q   V   Q   M   F   V   I   G   C   V   P   C   M   G   E   H     -

```
    TGGGACAAAGCTAAGGTTTGTGAATCAGAAGCAAATAATCAACAAGGCTTATGTCCACCC
181 ----------+----------+----------+----------+----------+----------+ 240
    ACCCTGTTTCGATTCCAAACACTTAGTCTTCGTTTATTAGTTGTTCCGAATACAGGTGGG
``` a      W   D   K   A   K   V   C   E   S   E   A   N   N   Q   Q   G   L   C   P   P     -

```
    ATAGAGTTAAAAAAATTCAGTAATTGAAGATGGAGATATGTTTGATATAGGCTTTGGAAAT
241 ----------+----------+----------+----------+----------+----------+ 300
    TATCTCAATTTTTTAAGTCATTAACTTCTACCTCTATACAAACTATATCCGAAACCTTTA
``` a      I   E   L   K   N   S   V   I   E   D   G   D   M   F   D   I   G   F   G   N     -

```
    ATTAATAACAAAGCACTATCTTATAACAAGTCAGATGTTAGTTTAGATATAGTTAATGAA
301 ----------+----------+----------+----------+----------+----------+ 360
    TAATTATTGTTTCGTGATAGAATATTGTTCAGTCTACAATCAAATCTATATCAATTACTT
``` a      I   N   N   K   A   L   S   Y   N   K   S   D   V   S   L   D   I   V   N   E     -

```
    GTGTGCAAATATCCAGACTTTTTAACCATGGCTAATGATGTGTATGGAGATGCTTGTTTT
361 ----------+----------+----------+----------+----------+----------+ 420
    CACACGTTTATAGGTCTGAAAAATTGGTACCGATTACTACACATACCTCTACGAACAAAA
``` a      V   C   K   Y   P   D   F   L   T   M   A   N   D   V   Y   G   D   A   C   F     -

```
    TTCTTTGCTAGACGAGAACAATGTTATGCCAGACATTATTTTGTTAGGGGAGGCAATGTT
421 ----------+----------+----------+----------+----------+----------+ 480
    AAGAAACGATCTGCTCTTGTTACAATACGGTCTGTAATAAAACAATCCCCTCCGTTACAA
``` a      F   F   A   R   R   E   Q   C   Y   A   R   H   Y   F   V   R   G   G   N   V     -

FIG. 5-B

```
      GGCGATGCAATCCCTGATGGAGCAGTACAACAGGATCACAACTATTATTTACCTGCACAA
  481 ---------+---------+---------+---------+---------+---------+ 540
      CCGCTACGTTAGGGACTACCTCGTCATGTTGTCCTAGTGTTGATAATAAATGGACGTGTT a       G  D  A  I  P  D  G  A  V  Q  Q  D  H  N  Y  Y  L  P  A  Q    -

AATGCACAGCAACAACACACCTTGGGAAATTCTATATATTATCCAACTGTTAGTGGGTCT
  541 ---------+---------+---------+---------+---------+---------+ 600
      TTACGTGTCGTTGTTGTGTGGAACCCTTTAAGATATATAATAGGTTGACAATCACCCAGA a       N  A  Q  Q  Q  H  T  L  G  N  S  I  Y  Y  P  T  V  S  G  S    -

CTTGTAACATCTGATGCTCAGTTATTTAATAGACCATTTTGGTTACAACGTGCTCAAGGA
  601 ---------+---------+---------+---------+---------+---------+ 660
      GAACATTGTAGACTACGAGTCAATAAATTATCTGGTAAAACCAATGTTGCACGAGTTCCT a       L  V  T  S  D  A  Q  L  F  N  R  P  F  W  L  Q  R  A  Q  G    -

CAAAACAACGGTAT
  661 ---------+---- 674
      GTTTTGTTGCCATA
```

FIG. 6-A

```
        GGTAGTGGGCAACCATTAGGTGTAGGCACCACAGGACATCCACTGTTTAATAAACTTAGA
     1  ------------+----------+----------+----------+----------+     60
        CCATCACCCGTTGGTAATCCACATCCGTGGTGTCCTGTAGGTGACAAATTATTTGAATCT a         G  S  G  Q  P  L  G  V  G  T  T  G  H  P  L  F  N  K  L  R     -

GATTCAGAAAATTCTGCAGAACGTCTGGAAGGAACAAGTGATGATAGGAGGAATATATCA
    61  ------------+----------+----------+----------+----------+    120
        CTAAGTCTTTTAAGACGTCTTGCAGACCTTCCTTGTTCACTACTATCCTCCTTATATAGT a         D  S  E  N  S  A  E  R  L  E  G  T  S  D  D  R  R  N  I  S     -

TTTGATCCTAAGCAAGTGCAAATGTTTGTGATAGGCTGCACCCCCTGTTTAGGGGAGTAT
   121  ------------+----------+----------+----------+----------+    180
        AAACTAGGATTCGTTCACGTTTACAAACACTATCCGACGTGGGGGACAAATCCCCTCATA a         F  D  P  K  Q  V  Q  M  F  V  I  G  C  T  P  C  L  G  E  Y     -

TGGGATACAGCTCCAGTATGTAAAGATGCAGGAAGTCAATTAGGCCTTTGCCCTCCATTA
   181  ------------+----------+----------+----------+----------+    240
        ACCCTATGTCGAGGTCATACATTTCTACGTCCTTCAGTTAATCCGGAAACGGGAGGTAAT a         W  D  T  A  P  V  C  K  D  A  G  S  Q  L  G  L  C  P  P  L     -

GAATTAAAAAACAGTGTTATAGAAGATGGCGATATGTTTGATATAGGATTTGGCAATATT
   241  ------------+----------+----------+----------+----------+    300
        CTTAATTTTTTGTCACAATATCTTCTACCGCTATACAAACTATATCCTAAACCGTTATAA a         E  L  K  N  S  V  I  E  D  G  D  M  F  D  I  G  F  G  N  I     -

AACAACAAAACATTAAGTTTTAATAAGTCAGATGTTAGTGTGGACATTGTTAATGAAATT
   301  ------------+----------+----------+----------+----------+    360
        TTGTTGTTTTGTAATTCAAAATTATTCAGTCTACAATCACACCTGTAACAATTACTTTAA a         N  N  K  T  L  S  F  N  K  S  D  V  S  V  D  I  V  N  E  I     -

TGTAAATATCCTGATTTTTTAACTATGTCCAATGATGTTTATGGAGACTCTTGCTTTTTC
   361  ------------+----------+----------+----------+----------+    420
        ACATTTATAGGACTAAAAAATTGATACAGGTTACTACAAATACCTCTGAGAACGAAAAAG a         C  K  Y  P  D  F  L  T  M  S  N  D  V  Y  G  D  S  C  F  F     -

TTTGCTCGCAGAGAGCGATGTTATGCAAGGCATTATTTTGTACGCGGAGGGGCAGTGGGT
   421  ------------+----------+----------+----------+----------+    480
        AAACGAGCGTCTCTCGCTACAATACGTTCCGTAATAAAACATGCGCCTCCCCGTCACCCA a         F  A  R  R  E  R  C  Y  A  R  H  Y  F  V  R  G  G  A  V  G     -
```

FIG. 6-B

```
    GATTTAATACCAGATGCTACAGTTAATCAGGACCATAAATATTACTTACCAGCAAATCCA
481 ---------+---------+---------+---------+---------+---------+ 540
    CTAAATTATGGTCTACGATGTCAATTAGTCCTGGTATTTATAATGAATGGTCGTTTAGGT a    D  L  I  P  D  A  T  V  N  Q  D  H  K  Y  Y  L  P  A  N  P   -

CCTGCCACATTGGAAAACTCTACATACTTTCCGACTGCTAGTGGCTCCTTAGTGACATCT
541 ---------+---------+---------+---------+---------+---------+ 600
    GGACGGTGTAACCTTTTGAGATGTATGAAAGGCTGACGATCACCGAGGAATCACTGTAGA a    P  A  T  L  E  N  S  T  Y  F  P  T  A  S  G  S  L  V  T  S   -

GATGCACAATTATTTAATAGGCCCTTTTGGTTAAAACGTGCACAAGGTCATAATAATGGT
601 ---------+---------+---------+---------+---------+---------+ 660
    CTACGTGTTAATAAATTATCCGGGAAAACCAATTTTGCACGTGTTCCAGTATTATTACCA a    D  A  Q  L  F  N  R  P  F  W  L  K  R  A  Q  G  H  N  N  G   -

```
        GGTAGGGGGCAACCATTTGGGGTAGGCACTACAGGTCATCCATTATTTAACAAATTACGT
     1  ----------+----------+----------+----------+----------+----------+  60
        CCATCCCCCGTTGGTAAACCCCATCCGTGATGTCCAGTAGGTAATAAATTGTTTAATGCA a       G  R  G  Q  P  F  G  V  G  T  T  G  H  P  L  F  N  K  L  R     -

GATGCAGAAAATTCCAGCGAACGTCAGGGAGATACTGCTGCAGATGACAGAATGAATATA
    61  ----------+----------+----------+----------+----------+----------+  120
        CTACGTCTTTTAAGGTCGCTTGCAGTCCCTCTATGACGACGTCTACTGTCTTACTTATAT a       D  A  E  N  S  S  E  R  Q  G  D  T  A  A  D  D  R  M  N  I     -

TCTTTTGATCCTAAGCAGGTACAAATGTTCATAATAGGTTGCACACCGTGTTTAGGTGAA
   121  ----------+----------+----------+----------+----------+----------+  180
        AGAAAACTAGGATTCGTCCATGTTTACAAGTATTATCCAACGTGTGGCACAAATCCACTT a       S  F  D  P  K  Q  V  Q  M  F  I  I  G  C  T  P  C  L  G  E     -

TATTGGGATCAAGCGCCTGTATGTAAAGATGCAGGTAACCAAATGGGCTTATGTCCTCCT
   181  ----------+----------+----------+----------+----------+----------+  240
        ATAACCCTAGTTCGCGGACATACATTTCTACGTCCATTGGTTTACCCGAATACAGGAGGA a       Y  W  D  Q  A  P  V  C  K  D  A  G  N  Q  M  G  L  C  P  P     -

CTTGAACTAAAGAATAGTGTCATAGAAGATGGAGATATGTTTGATATAGGCTTTGGTAAC
   241  ----------+----------+----------+----------+----------+----------+  300
        GAACTTGATTTCTTATCACAGTATCTTCTACCTCTATACAAACTATATCCGAAACCATTG a       L  E  L  K  N  S  V  I  E  D  G  D  M  F  D  I  G  F  G  N     -

ATTAATAATAAGACACTGTCATTCAATAGATCAGATGTTAGTTTAGATATTGTAAATGAA
   301  ----------+----------+----------+----------+----------+----------+  360
        TAATTATTATTCTGTGACAGTAAGTTATCTAGTCTACAATCAAATCTATAACATTTACTT a       I  N  N  K  T  L  S  F  N  R  S  D  V  S  L  D  I  V  N  E     -

ATATGCAAATATCCAGATTTTTTAACAATGTCCAATGATGTTTATGGTGACTCCTGTTTT
   361  ----------+----------+----------+----------+----------+----------+  420
        TATACGTTTATAGGTCTAAAAAATTGTTACAGGTTACTACAAATACCACTGAGGACAAAA a       I  C  K  Y  P  D  F  L  T  M  S  N  D  V  Y  G  D  S  C  F     -

TTTTGTGCTCGAAGAGAGCAATGTTATGCTAGACATTATTTTGTACGAGGCGGTGTTGTT
   421  ----------+----------+----------+----------+----------+----------+  480
        AAAACACGAGCTTCTCTCGTTACAATACGATCTGTAATAAAACATGCTCCGCCACAACAA a       F  C  A  R  R  E  Q  C  Y  A  R  H  Y  F  V  R  G  G  V  V     -
```

FIG. 7-B

```
    GGAGATTCTATACCAGACGGTGCAGTCCAGCAGAGTAACAAATATTATTTAGCTTCAGCT
481 ----------+---------+---------+---------+---------+---------+ 540
    CCTCTAAGATATGGTCTGCCACGTCAGGTCGTCTCATTGTTTATAATAAATCGAAGTCGA a     G  D  S  I  P  D  G  A  V  Q  Q  S  N  K  Y  Y  L  A  S  A   -

CAAAATAATAGCTTGGAAAATTCTACCTATTTCCCAACTGTAAGTGGTTCTTTAGTGACT
541 ----------+---------+---------+---------+---------+---------+ 600
    GTTTTATTATCGAACCTTTTAAGATGGATAAAGGGTTGACATTCACCAAGAAATCACTGA a     Q  N  N  S  L  E  N  S  T  Y  F  P  T  V  S  G  S  L  V  T   -

TCTGATGCTCAGCTATTTAACAGACCCTTTTGGTTAAAGCGTGCTCAAGGGCATAATAAT
601 ----------+---------+---------+---------+---------+---------+ 660
    AGACTACGAGTCGATAAATTGTCTGGGAAAACCAATTTCGCACGAGTTCCCGTATTATTA a     S  D  A  Q  L  F  N  R  P  F  W  L  K  R  A  Q  G  H  N  N   -

GGAAT
661 ----- 665
    CCTTA
```

FIG. 8-A

```
    GGAAGAGGTCTCCATTTGGGTGTAGGTACAGCAGGCCATCCACTATTCAATAAAGTTAGA
  1 ----------+----------+----------+----------+----------+----------+  60
    CCTTCTCCAGAGGTAAACCCACATCCATGTCGTCCGGTAGGTGATAAGTTATTTCAATCT a    G  R  G  L  H  L  G  V  G  T  A  G  H  P  L  F  N  K  V  R     -

GATACAGAAAATAATAGTGGCTATCAAGATACGTCTACGGATGACAGACAAAATACATCA
 61 ----------+----------+----------+----------+----------+----------+ 120
    CTATGTCTTTTATTATCACCGATAGTTCTATGCAGATGCCTACTGTCTGTTTTATGTAGT a    D  T  E  N  N  S  G  Y  Q  D  T  S  T  D  D  R  Q  N  T  S     -

TTTGATCCAAAACAAGTTCAAATGTTTGTAGTAGGATGTGCTCCTTGTTTGGGAGAACAT
121 ----------+----------+----------+----------+----------+----------+ 180
    AAACTAGGTTTTGTTCAAGTTTACAAACATCATCCTACACGAGGAACAAACCCTCTTGTA a    F  D  P  K  Q  V  Q  M  F  V  V  G  C  A  P  C  L  G  E  H     -

TGGGATAAAGCTCCTGTCTGTGACTCAGATAAAAATAACCAGGCTGGAAAATGCCCTCCA
181 ----------+----------+----------+----------+----------+----------+ 240
    ACCCTATTTCGAGGACAGACACTGAGTCTATTTTTATTGGTCCGACCTTTTACGGGAGGT a    W  D  K  A  P  V  C  D  S  D  K  N  N  Q  A  G  K  C  P  P     -

TTAGAACTGAGAAACACAGTAATAGAAGATGGAGATATGATTGATATAGGCTTTGGCAAT
241 ----------+----------+----------+----------+----------+----------+ 300
    AATCTTGACTCTTTGTGTCATTATCTTCTACCTCTATACTAACTATATCCGAAACCGTTA a    L  E  L  R  N  T  V  I  E  D  G  D  M  I  D  I  G  F  G  N     -

ATAAACAACAAGGTTTTATCAGTTACTAAGTCAGATGTTAGTCTGGATATAGTTAATGAA
301 ----------+----------+----------+----------+----------+----------+ 360
    TATTTGTTGTTCCAAAATAGTCAATGATTCAGTCTACAATCAGACCTATATCAATTACTT a    I  N  N  K  V  L  S  V  T  K  S  D  V  S  L  D  I  V  N  E     -

ACTTGTAAGTATCCAGATTTTTTAACTATGGCCAATGATGTATATGGTGACTCTTGTTTT
361 ----------+----------+----------+----------+----------+----------+ 420
    TGAACATTCATAGGTCTAAAAAATTGATACCGGTTACTACATATACCACTGAGAACAAAA a    T  C  K  Y  P  D  F  L  T  M  A  N  D  V  Y  G  D  S  C  F     -

TTCTTTGCAAGGAGAGAACAGTGTTATGCTAGACATTATTATGTTAGGGGAGGTGTAGTA
421 ----------+----------+----------+----------+----------+----------+ 480
    AAGAAACGTTCCTCTCTTGTCACAATACGATCTGTAATAATACAATCCCCTCCACATCAT a    F  F  A  R  R  E  Q  C  Y  A  R  H  Y  Y  V  R  G  G  V  V     -
```

FIG. 8-B

```
    GGTGATGCTATTCCTGATGAAGCTGTGAATCAAGATAAAAACTTTGTGTTACCTGCACAA
481 ----------+----------+----------+----------+----------+---------+ 540
    CCACTACGATAAGGACTACTTCGACACTTAGTTCTATTTTTGAAACACAATGGACGTGTT a     G  D  A  I  P  D  E  A  V  N  Q  D  K  N  F  V  L  P  A  Q   -

GGCACTCAGCAACAAAAGGATATAGCTAGTTCTATATATTTTCCAACTGTTAGTGGTTCC
541 ----------+----------+----------+----------+----------+---------+ 600
    CCGTGAGTCGTTGTTTTCCTATATCGATCAAGATATATAAAAGGTTGACAATCACCAAGG a     G  T  Q  Q  Q  K  D  I  A  S  S  I  Y  F  P  T  V  S  G  S   -

TTAGTAACTTCTGATGCTCAATTATTTAACAGACCATTTTGGTTACGCAGAGCACAAGGG
601 ----------+----------+----------+----------+----------+---------+ 660
    AATCATTGAAGACTACGAGTTAATAAATTGTCTGGTAAAACCAATGCGTCTCGTGTTCCC a     L  V  T  S  D  A  Q  L  F  N  R  P  F  W  L  R  R  A  Q  G   -

CAAAATAACGGGAT
661 ----------+---- 674
    GTTTTATTGCCCTA
```

FIG. 9-A

```
         GGGAGAGGACAGCCATTAGGCGTTGGTACCAGTGGACATCCACTGTTTAACAAAGTTAAT
    1    ----------+----------+----------+----------+----------+----------+    60
         CCCTCTCCTGTCGGTAATCCGCAACCATGGTCACCTGTAGGTGACAAATTGTTTCAATTA a         G  R  G  Q  P  L  G  V  G  T  S  G  H  P  L  F  N  K  V  N       -

GATGCCGAAAATCCCTTAGCTTACAGGGCACAGGCCTTTTCTACTGATGATAGGCAAAAC
   61    ----------+----------+----------+----------+----------+----------+   120
         CTACGGCTTTTAGGGAATCGAATGTCCCGTGTCCGGAAAAGATGACTACTATCCGTTTTG a         D  A  E  N  P  L  A  Y  R  A  Q  A  F  S  T  D  D  R  Q  N       -

ACATCCTTTGATCCTAAACAAATACAAATGTTTATAATAGGTTGTGCACCCTGTATTGGA
  121    ----------+----------+----------+----------+----------+----------+   180
         TGTAGGAAACTAGGATTTGTTTATGTTTACAAATATTATCCAACACGTGGGACATAACCT a         T  S  F  D  P  K  Q  I  Q  M  F  I  I  G  C  A  P  C  I  G       -

GAGCATTGGGATGTAGGTGAACGTTGTGCAGGAGCCAATAATGAAAATGGTCGATGCCCC
  181    ----------+----------+----------+----------+----------+----------+   240
         CTCGTAACCCTACATCCACTTGCAACACGTCCTCGGTTATTACTTTTACCAGCTACGGGG a         E  H  W  D  V  G  E  R  C  A  G  A  N  N  E  N  G  R  C  P       -

CCTATTAAATTGGTAAATTCAGTCATCCAAGATGGAGATATGGCAGATATTGGTTATGGA
  241    ----------+----------+----------+----------+----------+----------+   300
         GGATAATTTAACCATTTAAGTCAGTAGGTTCTACCTCTATACCGTCTATAACCAATACCT a         P  I  K  L  V  N  S  V  I  Q  D  G  D  M  A  D  I  G  Y  G       -

AACCTAAATTTCCGTACCTTACAGGAAAACAGATCTGATGTAAGTTTAGATATAGTGAAT
  301    ----------+----------+----------+----------+----------+----------+   360
         TTGGATTTAAAGGCATGGAATGTCCTTTTGTCTAGACTACATTCAAATCTATATCACTTA a         N  L  N  F  R  T  L  Q  E  N  R  S  D  V  S  L  D  I  V  N       -

GAAACCTGTAAATATCCAGACTTTTTAAAGATGCAGAATGATATATATGGCGATTCTTGC
  361    ----------+----------+----------+----------+----------+----------+   420
         CTTTGGACATTTATAGGTCTGAAAAATTTCTACGTCTTACTATATATACCGCTAAGAACG a         E  T  C  K  Y  P  D  F  L  K  M  Q  N  D  I  Y  G  D  S  C       -

TTTTTCTTTGCTCGCCGGGAGCAATGTTATGCAAGACATTTTTTTGTTCGTGGGGGTAAG
  421    ----------+----------+----------+----------+----------+----------+   480
         AAAAAGAAACGAGCGGCCCTCGTTACAATACGTTCTGTAAAAAAACAAGCACCCCCATTC a         F  F  F  A  R  R  E  Q  C  Y  A  R  H  F  F  V  R  G  G  K       -
```

FIG. 9-B

```
    GCGGGGGATGACATTCCTGGTGCGCAAATCGATGCAGGTACATATAAAAATGATTTTTAC
481 ---------+---------+---------+---------+---------+---------+ 540
    CGCCCCCTACTGTAAGGACCACGCGTTTAGCTACGTCCATGTATATTTTTACTAAAAATG a    A  G  D  D  I  P  G  A  Q  I  D  A  G  T  Y  K  N  D  F  Y  -

ATACCTGGAGCGTCAGGTCAGACACAAAAGAATATAGGTAACTCGATGTATTTCCCAACA
541 ---------+---------+---------+---------+---------+---------+ 600
    TATGGACCTCGCAGTCCAGTCTGTGTTTTCTTATATCCATTGAGCTACATAAAGGGTTGT a    I  P  G  A  S  G  Q  T  Q  K  N  I  G  N  S  M  Y  F  P  T  -

GTAAGTGGCTCATTGGTGTCTAGTGATGCTCAATTGTTTAATAGGCCCTTCTGGCTCCAA
601 ---------+---------+---------+---------+---------+---------+ 660
    CATTCACCGAGTAACCACAGATCACTACGAGTTAACAAATTATCCGGGAAGACCGAGGTT a    V  S  G  S  L  V  S  S  D  A  Q  L  F  N  R  P  F  W  L  Q  -

CGGGCGCAGGGGCAAAACAACGGAAT
661 ---------+---------+------ 686
    GCCCGCGTCCCCGTTTTGTTGCCTTA
```

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
    (A) LENGTH: 647 base pairs
    (B) TYPE: nucleic acid
    (C) STRANDEDNESS: double
    (D) TOPOLOGY: linear (ii) MOLECULE TYPE: DNA (ix) FEATURE:
    (A) NAME/KEY: CDS
    (B) LOCATION: 1 .. 645

(xi) SEQUENCE DESCRIPTION: SEQ ID NO: 1:

```
GGT AGA GGA CAG CCA TTA GGC GTG GGG TTA A GT GGA CAC CCT CTG TAT       48
Gly Arg Gly Gln Pro Leu Gly Val Gly Leu S er Gly His Pro Leu Tyr
 1               5                  10                  15

AAC AAA CTG AAT GAC ACT GAA AAC TCC AAC A TT GCA CAT GCT GAC AAT       96
Asn Lys Leu Asn Asp Thr Glu Asn Ser Asn I le Ala His Asn Asp Asn
             20                  25                  30

AGT CCT GAC TCC CGG GAC AAC ATT TCT GTT G AC TGT AAG CAA ACA CAA      144
Ser Pro Asp Ser Arg Asp Asn Ile Ser Val A sp Cys Lys Gln Thr Gln
         35                  40                  45

CTG TGC ATA CTG GGC TGT ACG CCC CCC ATG G GG GAA TAC TGG GGT AAG      192
Leu Cys Ile Leu Gly Cys Thr Pro Pro Met G ly Glu Tyr Trp Gly Lys
     50                  55                  60

GGT ACC CCT TGT GCA CGT ACT AAT ACT ACC C CA GGA GAC TGT CCT CCC      240
Gly Thr Pro Cys Ala Arg Thr Asn Thr Thr P ro Gly Asp Cys Pro Pro
 65                  70                  75                  80

TTG GAG TTA ATG ACA TCT TAT ATT CAG GAT G GC GAC ATG GTG GAT ACC      288
Leu Glu Leu Met Thr Ser Tyr Ile Gln Asp G ly Asp Met Val Asp Thr
                 85                  90                  95

GGG TAT GGT GCC ATG GAC TTT ACT GCC CTG C AA TTT AAT AAG TCT GAC      336
Gly Tyr Gly Ala Met Asp Phe Thr Ala Leu G ln Phe Asn Lys Ser Asp
            100                 105                 110

GTG CCC CTT GAT ATT TGC CAG TCT ATT TGC A AA TAT CCC GAT TAT TTG      384
Val Pro Leu Asp Ile Cys Gln Ser Ile Cys L ys Tyr Pro Asp Tyr Leu
            115                 120                 125

GGC ATG GCT GCC GAC CCG TAT GGC GAT AGC A TG TTC TTT TTC CTC CGT      432
Gly Met Ala Ala Asp Pro Tyr Gly Asp Ser M et Phe Phe Phe Leu Arg
        130                 135                 140

CGG GAA CAA CTG TTT GCC AGA CAC TTT TTC A AT CGT GCG GGT GAT GTT      480
Arg Glu Gln Leu Phe Ala Arg His Phe Phe A sn Arg Ala Gly Asp Val
145                 150                 155                 160

GGA GAC AAA ATT CCA GAA TCT TTG TAC CTC A AA GGG AGT AGC GGG CGT      528
Gly Asp Lys Ile Pro Glu Ser Leu Tyr Leu L ys Gly Ser Ser Gly Arg
                165                 170                 175

GAG ACT CCC GGC AGT GCT ATA TAC AGC CCC A CA CCC AGT GGG TCT ATG      576
Glu Thr Pro Gly Ser Ala Ile Tyr Ser Pro T hr Pro Ser Gly Ser Met
            180                 185                 190

GTG ACC TCT GAG GCA CAA ATA TTC AAT AAG T CT TAC TGG CTA CAG CAA      624
Val Thr Ser Glu Ala Gln Ile Phe Asn Lys S er Tyr Trp Leu Gln Gln
        195                 200                 205

GCT CAA GGC CAA AAT AAC GGT AT                                        647
Ala Gln Gly Gln Asn Asn Gly
        210                 215
```

(2) INFORMATION FOR SEQ ID NO: 2:

(i) SEQUENCE CHARACTERISTICS:
        (A) LENGTH: 668 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 666

(xi) SEQUENCE DESCRIPTION: SEQ ID NO: 2:

```
TCA AGA GGA CAC CCA TTA GGA GTA GGG TCT A CA GGT CAT CCC CTA TTT      48
Ser Arg Gly His Pro Leu Gly Val Gly Ser T hr Gly His Pro Leu Phe
 1               5                  10                  15

AAT AAA GTG AAG GAT ACG GAA AAT GCT AAT A AT TAT ATA GTA ACA TCT      96
Asn Lys Val Lys Asp Thr Glu Asn Ala Asn A sn Tyr Ile Val Thr Ser
            20                  25                  30

AAG GAT GAT AGG CAG GAC ACC TCA TTT GAT C CT AAA CAG GTT CAA ATG     144
Lys Asp Asp Arg Gln Asp Thr Ser Phe Asp P ro Lys Gln Val Gln Met
        35                  40                  45

TTT ATT ATT GGC TGC GCA CCG TGC ATA GGT G AG CAC TGG GAT GCA GCC     192
Phe Ile Ile Gly Cys Ala Pro Cys Ile Gly G lu His Trp Asp Ala Ala
    50                  55                  60

AAG CCC TGT GAT GCT GAC AGA GGG GTA GGC A AA TGT CCA CCT TTG GAA     240
Lys Pro Cys Asp Ala Asp Arg Gly Val Gly L ys Cys Pro Pro Lys Glu
65                  70                  75                  80

CTG GTA AAT ACT GTA ATA GAA GAT GGA GAT A TG GTG GAT ATA GGT TTT     288
Leu Val Asn Thr Val Ile Glu Asp Gly Asp M et Val Asp Ile Gly Phe
                85                  90                  95

GGA AAT ATA AAT AAT AAA ACC CTG TCA GCA A AT AAG TCA GAT GTC AGT     336
Gly Asn Ile Asn Asn Lys Thr Leu Ser Ala A sn Lys Ser Asp Val Ser
            100                 105                 110

TTA GAT ATA GTT AAT AAT ATT TGT AAG TAT C CA GAC TTT TTA AAA ATG     384
Leu Asp Ile Val Asn Asn Ile Cys Lys Tyr P ro Asp Phe Leu Lys Met
        115                 120                 125

GCC AAT GAC ATA TAT GGA GAC TCC TGT TTT T TT TAT GCT AGA CGG GAG     432
Ala Asn Asp Ile Tyr Gly Asp Ser Cys Phe P he Tyr Ala Arg Arg Glu
    130                 135                 140

CAA TGT TAT GCT AGA CAT TTT TTT GTT AGA G GA GGT AAT GTA GGA GAT     480
Gln Cys Tyr Ala Arg His Phe Phe Val Arg G ly Gly Asn Val Gly Asp
145                 150                 155                 160

GCT ATT CCT GAT GCT GCA GTG GGT CAG GAC A AT AAC TTT GTG TTG CCT     528
Ala Ile Pro Asp Ala Ala Val Gly Gln Asp A sn Asn Phe Val Leu Pro
                165                 170                 175

GCA GCT GTT GGA CAG GCC CAA AAC ACT TTG G GT AGC TCT ATT TAC GTG     576
Ala Ala Val Gly Gln Ala Gln Asn Thr Leu G ly Ser Ser Ile Tyr Val
            180                 185                 190

CCT ACC GTT AGT GGT TCT TTG GTA TCC ACA G AT GCA CAA TTA TTT AAT     624
Pro Thr Val Ser Gly Ser Leu Val Ser Thr A sp Ala Gln Leu Phe Asn
        195                 200                 205

AGG CCC TTT TGG CTA CAA CGA GCA CAG GGT C AT AAT AAC GGT AT         668
Arg Pro Phe Trp Leu Gln Arg Ala Gln Gly H is Asn Asn Gly
    210                 215                 220
```

(2) INFORMATION FOR SEQ ID NO: 3:

(i) SEQUENCE CHARACTERISTICS:
        (A) LENGTH: 661 base pairs (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 660

(xi) SEQUENCE DESCRIPTION: SEQ ID NO: 3:

```
TCT AGG GGG CAA CCC TTG GGG GTA GGT TCT A CA GGC CAT CCT TTG TTC        48
Ser Arg Gly Gln Pro Leu Gly Val Gly Ser T hr Gly His Pro Leu Phe
 1               5                  10                  15

AAT AAA GTA AAG GAT ACT GAA AAT TCA AAT A AT TAT ATA ACA ATG TCT        96
Asn Lys Val Lys Asp Thr Glu Asn Ser Asn A sn Tyr Ile Thr Met Ser
                20                  25                  30

AAA GAT GAT AGG CAG GAC ACC TCG TTT GAC C CT AAG CAG GTT CAA ATG       144
Lys Asp Asp Arg Gln Asp Thr Ser Phe Asp P ro Lys Gln Val Gln Met
            35                  40                  45

TTT ATT ATT GGC TGT GCA CCT TGT ATA GGG G AG CAC TGG GAT GCT GCC       192
Phe Ile Ile Gly Cys Ala Pro Cys Ile Gly G lu His Trp Asp Ala Ala
        50                  55                  60

AAA CCC TGT GAC GCT GAC AAA GGA GAC GGT A AA TGT CCA CCT TTA GAA       240
Lys Pro Cys Asp Ala Asp Lys Gly Asp Gly L ys Cys Pro Pro Leu Glu
 65                 70                  75                  80

TTA GTA AAT ACA GTT ATT GAG GAT GGG GAT A TG GTG GAT ATA GGT TTT       288
Leu Val Asn Thr Val Ile Glu Asp Gly Asp M et Val Asp Ile Gly Phe
                85                  90                  95

GGT AAC ATA AAT AAT AAA ACC TTG TCA GCA A AT AAA TCA GAT GTC AGT       336
Gly Asn Ile Asn Asn Lys Thr Leu Ser Ala A sn Lys Ser Asp Val Ser
            100                 105                 110

TTG GAT ATA GTT AAT AAC ATT TGT AAG TAT C CA GAC TTC CTT AAA ATG       384
Leu Asp Ile Val Asn Asn Ile Cys Lys Tyr P ro Asp Phe Leu Lys Met
        115                 120                 125

GCC AAT GAC ATA TAT GGG GAC TCC TGT TTT T TT TAT GCC AGG CGG GAA       432
Ala Asn Asp Ile Tyr Gly Asp Ser Cys Phe P he Tyr Ala Arg Arg Glu
    130                 135                 140

CAA TGT TAT GCT AGA CAC TTT TTT GTT AGG G GA GGC AAT GTA GGC GAT       480
Gln Cys Tyr Ala Arg His Phe Phe Val Arg G ly Gly Asn Val Gly Asp
145                 150                 155                 160

CGA ATT CCT AAT GCT GCA GTG GGT CAG GAC A AT AAT TTT ATG TTA CCT       528
Arg Ile Pro Asn Ala Ala Val Gly Gln Asp A sn Asn Phe Met Leu Pro
                165                 170                 175

GCA GCC GCT GGG CAG GCT CAA AAC ACT TTG G GC AAC TCT ATT TAT GTT       576
Ala Ala Ala Gly Gln Ala Gln Asn Thr Leu G ly Asn Ser Ile Tyr Val
            180                 185                 190

CCC ACG TCA AGT GGT TCT TTG GTG TCC ACA G AT GCT CAA TTA TTT AAC       624
Pro Thr Val Ser Gly Ser Leu Val Ser Thr A sp Ala Gln Leu Phe Asn
        195                 200                 205

AGG CCA TTT TGG CTG CAA CGA GCA CAA GGT C AC AAC A                     661
Arg Pro Phe Trp Leu Gln Arg Ala Gln Gly H is Asn
    210                 215                 220
```

(2) INFORMATION FOR SEQ ID NO: 4:

(i) SEQUENCE CHARACTERISTICS:
        (A) LENGTH: 677 base pairs
        (B) TYPE: nucleic acid
        (C) STRANDEDNESS: double
        (D) TOPOLOGY: linear (ii) MOLECULE TYPE: DNA (ix) FEATURE:
    (A) NAME/KEY: CDS
    (B) LOCATION: 1 .. 675

(xi) SEQUENCE DESCRIPTION: SEQ ID NO: 4:

| | | | | | | | | | | | | | | | | |
|---|---|---|---|---|---|---|---|---|---|---|---|---|---|---|---|---|
| GGA | AGT | GGT | CTT | CCA | TTA | GGC | ATA | GGC | AGC | A GT | GGT | CAC | CCT | CTG | TTT | 48 |
| Gly | Ser | Gly | Leu | Pro | Leu | Gly | Ile | Gly | Ser | S er | Gly | His | Pro | Leu | Phe | |
| 1 | | | | 5 | | | | | 10 | | | | | 15 | | |
| AAC | AAG | GTA | AAT | GAT | ACA | GAA | AAT | GGC | AAC | A CA | TAT | AAA | GGG | ACA | ACT | 96 |
| Asn | Lys | Val | Asn | Asp | Thr | Glu | Asn | Gly | Asn | T hr | Tyr | Lys | Gly | Thr | Thr | |
| | | | 20 | | | | | 25 | | | | | 30 | | | |
| AAA | GAT | GAT | AGA | CAA | AAC | ATT | TCA | TTT | GAT | C CT | AAA | CAA | TTA | CAG | ATG | 144 |
| Lys | Asp | Asp | Arg | Gln | Asn | Ile | Ser | Phe | Asp | P ro | Lys | Gln | Leu | Gln | Met | |
| | | | 35 | | | | | 40 | | | | | 45 | | | |
| TTT | ATA | ATT | GGC | TGT | ACA | CCA | TGT | ATT | GGT | G AA | CAT | TGG | GAT | AAG | GCT | 192 |
| Phe | Ile | Ile | Gly | Cys | Thr | Pro | Cys | Ile | Gly | G lu | His | Trp | Asp | Lys | Ala | |
| 50 | | | | | 55 | | | | | 60 | | | | | | |
| CCT | GCA | TGT | GTT | AAT | GAT | ATT | CAA | CAA | GGT | A GT | TGC | CCA | CCA | ATA | GAA | 240 |
| Pro | Ala | Lys | Val | Asn | Asp | Ile | Gln | Gln | Gly | S er | Cys | Pro | Pro | Ile | Glu | |
| 65 | | | | 70 | | | | | 75 | | | | | 80 | | |
| TTA | GTT | AAC | ACA | TAC | ATA | CAG | GGT | GGA | GAT | A TG | GCT | GAT | ATA | GGA | TAT | 288 |
| Leu | Val | Asn | Thr | Tyr | Ile | Gln | Gly | Gly | Asp | M et | Ala | Asp | Ile | Gly | Tyr | |
| | | | | 85 | | | | | 90 | | | | | 95 | | |
| GGC | AAT | CTA | AAT | TTT | AAA | GCT | TTA | CAG | CAA | A AT | AGA | TCA | GAT | GTT | AGC | 336 |
| Gly | Asn | Leu | Asn | Phe | Lys | Ala | Leu | Gln | Gln | A sn | Arg | Ser | Asp | Val | Ser | |
| | | | 100 | | | | | 105 | | | | | 110 | | | |
| TTG | GAT | ATT | GTA | GAT | GAA | ATA | TGC | AAA | TAT | C CT | GAC | TTT | TTA | CGA | ATG | 384 |
| Leu | Asp | Ile | Val | Asp | Glu | Ile | Cys | Lys | Tyr | P ro | Asp | Phe | Leu | Arg | Met | |
| | | 115 | | | | | 120 | | | | | 125 | | | | |
| CAA | AAT | GAT | GTA | TAT | GGC | GAT | GCC | TGT | TTT | T TT | TAT | GCT | CGA | CGG | GAG | 432 |
| Gln | Asn | Asp | Val | Tyr | Gly | Asp | Ala | Cys | Phe | P he | Tyr | Ala | Arg | Arg | Glu | |
| | 130 | | | | | 135 | | | | | 140 | | | | | |
| CAA | TGT | TAT | GCC | AGG | CAC | TTT | TTT | GTG | CGT | G GT | GGC | AAA | CCT | GGT | GAT | 480 |
| Gln | Cys | Tyr | Ala | Arg | His | Phe | Phe | Val | Arg | G ly | Gly | Lys | Pro | Gly | Asp | |
| 145 | | | | | 150 | | | | | 155 | | | | | 160 | |
| GAT | ATA | CCT | GGT | GCC | CAA | ATT | GAT | GCA | GGG | T CA | CAT | AAA | AAT | GAA | TAT | 528 |
| Asp | Ile | Pro | Gly | Ala | Gln | Ile | Asp | Ala | Gly | S er | His | Lys | Asn | Glu | Tyr | |
| | | | 165 | | | | | 170 | | | | | 175 | | | |
| TAC | ATA | CAG | GCA | GCT | TCA | GAC | CAA | TCA | CAA | A AT | AGT | TTG | GGG | AAT | TCT | 576 |
| Tyr | Ile | Gln | Ala | Ala | Ser | Asp | Gln | Ser | Gln | A sn | Ser | Leu | Gly | Asn | Ser | |
| | | | 180 | | | | | 185 | | | | | 190 | | | |
| ATG | TAT | TTC | CCA | ACT | ATC | AGT | GGC | TCA | TTA | G TT | TCA | AGT | GAT | GCT | CAA | 624 |
| Met | Tyr | Phe | Pro | Thr | Ile | Ser | Gly | Ser | Leu | V al | Ser | Ser | Asp | Ala | Gln | |
| | | 195 | | | | | 200 | | | | | 205 | | | | |
| TTA | TTT | AAT | AGG | CCC | TTC | TGG | CTA | CAG | CGA | G CA | CAA | GGC | CAA | AAC | AAC | 672 |
| Leu | Phe | Asn | Arg | Pro | Phe | Trp | Leu | Gln | Arg | A la | Gln | Gly | Gln | Asn | Asn | |
| | 210 | | | | | 215 | | | | | 220 | | | | | |
| GGG | AT | | | | | | | | | | | | | | | 677 |
| Gly | | | | | | | | | | | | | | | | |
| 225 | | | | | | | | | | | | | | | | |

(2) INFORMATION FOR SEQ ID NO: 5:

(i) SEQUENCE CHARACTERISTICS:
        (A) LENGTH: 674 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS (B) LOCATION: 1 .. 672

(xi) SEQUENCE DESCRIPTION: SEQ ID NO: 5:

```
TCA AGG GGA CAG CCA TTG GGT GTA GGA ACA T CA GGT CAT CCT TTA TTT      48
Ser Arg Gly Gln Pro Leu Gly Val Gly Thr S er Gly His Pro Leu Phe
1               5                   10                  15

AAC AAA GTC AGG GAT ACT GAA AAC TCA GGT A AC TAT CAA GCA GTT TCT      96
Asn Lys Val Arg Asp Thr Glu Asn Ser Gly A sn Tyr Gln Ala Val Ser
            20                  25                  30

CAG GAT GAC AGA CAA AAT ACA TCT TTT GAT C CT AAA CAA GTG CAA ATG     144
Gln Asp Asp Arg Gln Asn Thr Ser Phe Asp P ro Lys Gln Val Gln Met
35                  40                  45

TTT GTC ATT GGC TGT GTG CCG TGT ATG GGT G AA CAT TGG GAC AAA GCT     192
Phe Val Ile Gly Cys Val Pro Cys Met Gly G lu His Trp Asp Lys Ala
    50                  55                  60

AAG GTT TGT GAA TCA GAA GCA AAT AAT CAA C AA GGC TTA TGT CCA CCC     240
Lys Val Cys Glu Ser Glu Ala Asn Asn Gln G ln Gly Leu Cys Pro Pro
65                  70                  75                  80

ATA GAG TTA AAA AAT TCA GTA ATT GAA GAT G GA GAT ATG TTT GAT ATA     288
Ile Glu Leu Lys Asn Ser Val Ile Glu Asp G ly Asp Met Phe Asp Ile
            85                  90                  95

GGC TTT GGA AAT ATT AAT AAC AAA GCA CTA T CT TAT AAC AAG TCA GAT     336
Gly Phe Gly Asn Ile Asn Asn Lys Ala Leu S er Tyr Asn Lys Ser Asp
                100                 105                 110

GTT AGT TTA GAT ATA GTT AAT GAA GTG TGC A AA TAT CCA GAC TTT TTA     384
Val Ser Leu Asp Ile Val Asn Glu Val Cys L ys Tyr Pro Asp Phe Leu
            115                 120                 125

ACC ATG GCT AAT GAT GTG TAT GGA GAT GCT T GT TTT TTC TTT GCT AGA     432
Thr Met Ala Asn Asp Val Tyr Gly Asp Ala C ys Phe Phe Phe Ala Arg
130                 135                 140

CGA GAA CAA TGT TAT GCC AGA CAT TAT TTT G TT AGG GGA GGC AAT GTT     480
Arg Glu Gln Cys Tyr Ala Arg His Tyr Phe V al Arg Gly Gly Asn Val
145                 150                 155                 160

GGC GAT GCA ATC CCT GAT GGA GCA GTA CAA C AG GAT CAC AAC TAT TAT     528
Gly Asp Ala Ile Pro Asp Gly Ala Val Gln G ln Asp His Asn Tyr Tyr
                165                 170                 175

TTA CCT GCA CAA AAT GCA CAG CAA CAA CAC A CC TTG GGA AAT TCT ATA     576
Leu Pro Ala Gln Asn Ala Gln Gln Gln His T hr Leu Gly Asn Ser Ile
            180                 185                 190

TAT TAT CCA ACT GTT AGT GGG TCT CTT GTA A CA TCT GAT GCT CAG TTA     624
Tyr Tyr Pro Thr Val Ser Gly Ser Leu Val T hr Ser Asp Ala Gln Leu
        195                 200                 205

TTT AAT AGA CCA TTT TGG TTA CAA CGT GCT C AA GGA CAA AAC AAC GGT     672
Phe Asn Arg Pro Phe Trp Leu Gln Arg Ala G ln Gly Gln Asn Asn Gly
210                 215                 220

AT                                                                    674
```

(2) INFORMATION FOR SEQ ID NO: 6:

(i) SEQUENCE CHARACTERISTICS:
        (A) LENGTH: 662 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 660

(xi) SEQUENCE DESCRIPTION: SEQ ID NO: 6:

-continued

```
GGT AGT GGG CAA CCA TTA GGT GTA GGC ACC A CA GGA CAT CCA CTG TTT          48
Gly Ser Gly Gln Pro Leu Gly Val Gly Thr T hr Gly His Pro Leu Phe
 1               5                  10                  15

AAT AAA CTT AGA GAT TCA GAA AAT TCT GCA G AA CGT CTG GAA GGA ACA          96
Asn Lys Leu Arg Asp Ser Glu Asn Ser Ala G lu Arg Leu Glu Gly Thr
             20                  25                  30

AGT GAT GAT AGG AGG AAT ATA TCA TTT GAT C CT AAG CAA GTG CAA ATG         144
Ser Asp Asp Arg Arg Asn Ile Ser Phe Asp P ro Lys Gln Val Gln Met
 35                  40                  45

TTT GTG ATA GGC TGC ACC CCC TGT TTA GGG G AG TAT TGG GAT ACA GCT         192
Phe Val Ile Gly Cys Thr Pro Cys Leu Gly G lu Tyr Trp Asp Thr Ala
         50                  55                  60

CCA GTA TGT AAA GAT GCA GGA AGT CAA TTA G GC CTT TGC CCT CCA TTA         240
Pro Val Cys Lys Asp Ala Gly Ser Gln Leu G ly Leu Cys Pro Pro Leu
 65                  70                  75                  80

GAA TTA AAA AAC AGT GTT ATA GAA GAT GGC G AT ATG TTT GAT ATA GGA         288
Glu Leu Lys Asn Ser Val Ile Glu Asp Gly A sp Met Phe Asp Ile Gly
                 85                  90                  95

TTT GGC AAT ATT AAC AAC AAA ACA TTA AGT T TT AAT AAG TCA GAT GTT         336
Phe Gly Asn Ile Asn Asn Lys Thr Leu Ser P he Asn Lys Ser Asp Val
             100                 105                 110

AGT GTG GAC ATT GTT AAT GAA ATT TGT AAA T AT CCT GAT TTT TTA ACT         384
Ser Val Asp Ile Val Asn Glu Ile Cys Lys T yr Pro Asp Phe Leu Thr
         115                 120                 125

ATG TCC AAT GAT GTT TAT GGA GAC TCT TGC T TT TTC TTT GCT CGC AGA         432
Met Ser Asn Asp Val Tyr Gly Asp Ser Cys P he Phe Phe Ala Arg Arg
 130                 135                 140

GAG CGA TGT TAT GCA AGG CAT TAT TTT GTA C GC GGA GGG GCA GTG GGT         480
Glu Arg Cys Tyr Ala Arg His Tyr Phe Val A rg Gly Gly Ala Val Gly
145                 150                 155                 160

GAT TTA ATA CCA GAT GCT ACA GTT AAT CAG G AC CAT AAA TAT TAC TTA         528
Asp Leu Ile Pro Asp Ala Thr Val Asn Gln A sp His Lys Tyr Tyr Leu
                 165                 170                 175

CCA GCA AAT CCA CCT GCC ACA TTG GAA AAC T CT ACA TAC TTT CCG ACT         576
Pro Ala Asn Pro Pro Ala Thr Leu Glu Asn S er Thr Tyr Phe Pro Thr
             180                 185                 190

GCT AGT GGC TCC TTA GTG ACA TCT GAT GCA C AA TTA TTT AAT AGG CCC         624
Ala Ser Gly Ser Leu Val Thr Ser Asp Ala G ln Leu Phe Asn Arg Pro
         195                 200                 205

TTT TGG TTA AAA CGT GCA CAA GGT CAT AAT A AT GGT AT                      662
Phe Trp Leu Lys Arg Ala Gln Gly His Asn A sn Gly
 210                 215                 220
```

(2) INFORMATION FOR SEQ ID NO: 7:

(i) SEQUENCE CHARACTERISTICS:
        (A) LENGTH: 665 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 663

(xi) SEQUENCE DESCRIPTION: SEQ ID NO: 7:

```
GGT AGG GGG CAA CCA TTT GGG GTA GGC ACT A CA GGT CAT CCA TTA TTT          48
Gly Arg Gly Gln Pro Phe Gly Val Gly Thr T hr Gly His Pro Leu Phe
 1               5                  10                  15

AAC AAA TTA CGT GAT GCA GAA AAT TCC AGC G AA CGT CAG GGA GAT ACT          96
Asn Lys Leu Arg Asp Ala Glu Asn Ser Ser G lu Arg Gln Gly Asp Thr
```

```
GCT GCA GAT GAC AGA ATG AAT ATA TCT TTT G AT CCT AAG CAG GTA CAA        144
Ala Ala Asp Asp Arg Met Asn Ile Ser Phe A sp Pro Lys Gln Val Gln
        35                      40                  45

ATG TTC ATA ATA GGT TGC ACA CCG TGT TTA G GT GAA TAT TGG GAT CAA        192
Met Phe Ile Ile Gly Cys Thr Pro Cys Leu G ly Glu Tyr Trp Asp Gln
    50                      55              60

GCG CCT GTA TGT AAA GAT GCA GGT AAC CAA A TG GGC TTA TGT CCT CCT        240
Ala Pro Val Cys Lys Asp Ala Gly Asn Gln M et Gly Leu Cys Pro Pro
65              70                      75                  80

CTT GAA CTA AAG AAT AGT GTC ATA GAA GAT G GA GAT ATG TTT GAT ATA        288
Leu Glu Leu Lys Asn Ser Val Ile Glu Asp G ly Asp Met Phe Asp Ile
            85                      90                  95

GGC TTT GGT AAC ATT AAT AAT AAG ACA CTG T CA TTC AAT AGA TCA GAT        336
Gly Phe Gly Asn Ile Asn Asn Lys Thr Leu S er Phe Asn Arg Ser Asp
                100                     105                 110

GTT AGT TTA GAT ATT GTA AAT GAA ATA TGC A AA TAT CCA GAT TTT TTA        384
Val Ser Leu Asp Ile Val Asn Glu Ile Cys L ys Tyr Pro Asp Phe Leu
            115                     120                 125

ACA ATG TCC AAT GAT GTT TAT GGT GAC TCC T GT TTT TTT TGT GCT CGA        432
Thr Met Ser Asn Asp Val Tyr Gly Asp Ser C ys Phe Phe Cys Ala Arg
        130                     135                 140

AGA GAG CAA TGT TAT GCT AGA CAT TAT TTT G TA CGA GGC GGT GTT GTT        480
Arg Glu Gln Cys Tyr Ala Arg His Tyr Phe V al Arg Gly Gly Val Val
145                 150                     155                 160

GGA GAT TCT ATA CCA GAC GGT GCA GTC CAG C AG AGT AAC AAA TAT TAT        528
Gly Asp Ser Ile Pro Asp Gly Ala Val Gln G ln Ser Asn Lys Tyr Tyr
                165                     170                 175

TTA GCT TCA GCT CAA AAT AAT AGC TTG GAA A AT TCT ACC TAT TTC CCA        576
Leu Ala Ser Ala Gln Asn Asn Ser Leu Glu A sn Ser Thr Tyr Phe Pro
            180                     185                 190

ACT GTA AGT GGT TCT TTA GTG ACT TCT GAT G CT CAG CTA TTT AAC AGA        624
Thr Val Ser Gly Ser Leu Val Thr Ser Asp A la Gln Leu Phe Asn Arg
        195                     200                 205

CCC TTT TGG TTA AAG CGT GCT CAA GGG CAT A AT AAT GGA AT                 665
Pro Phe Trp Leu Lys Arg Ala Gln Gly His A sn Asn Gly
    210                     215                 220

(2) INFORMATION FOR SEQ ID NO: 8:

(i) SEQUENCE CHARACTERISTICS:
        (A) LENGTH: 674 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 672

(xi) SEQUENCE DESCRIPTION: SEQ ID NO: 8:

GGA AGA GGT CTC CAT TTG GGT GTA GGT ACA G CA GGC CAT CCA CTA TTC         48
Gly Arg Gly Leu His Leu Gly Val Gly Thr A la Gly His Pro Leu Phe
1               5                       10                  15

AAT AAA GTT AGA GAT ACA GAA AAT AAT AGT G GC TAT CAA GAT ACG TCT         96
Asn Lys Val Arg Asp Thr Glu Asn Asn Ser G ly Tyr Gln Asp Thr Ser
            20                      25                  30

ACG GAT GAC AGA CAA AAT ACA TCA TTT GAT C CA AAA CAA GTT CAA ATG        144
Thr Asp Asp Arg Gln Asn Thr Ser Phe Asp P ro Lys Gln Val Gln Met
        35                      40                  45
```

```
TTT GTA GTA GGA TGT GCT CCT TGT TTG GGA G AA CAT TGG GAT AAA GCT         192
Phe Val Val Gly Cys Ala Pro Cys Leu Gly G lu His Trp Asp Lys Ala
         50                      55                     60

CCT GTC TGT GAC TCA GAT AAA AAT AAC CAG G CT GGA AAA TGC CCT CCA         240
Pro Val Cys Asp Ser Asp Lys Asn Asn Gln A la Gly Lys Cys Pro Pro
 65                      70                     75                  80

TTA GAA CTG AGA AAC ACA GTA ATA GAA GAT G GA GAT ATG ATT GAT ATA         288
Leu Glu Leu Arg Asn Thr Val Ile Glu Asp G ly Asp Met Ile Asp Ile
                     85                      90                     95

GGC TTT GGC AAT ATA AAC AAC AAG GTT TTA T CA GTT ACT AAG TCA GAT         336
Gly Phe Gly Asn Ile Asn Asn Lys Val Leu S er Val Thr Lys Ser Asp
                    100                     105                    110

GTT AGT CTG GAT ATA GTT AAT GAA ACT TGT A AG TAT CCA GAT TTT TTA         384
Val Ser Leu Asp Ile Val Asn Glu Thr Cys L ys Tyr Pro Asp Phe Leu
115                     120                     125

ACT ATG GCC AAT GAT GTA TAT GGT GAC TCT T GT TTT TTC TTT GCA AGG         432
Thr Met Ala Asn Asp Val Tyr Gly Asp Ser C ys Phe Phe Phe Ala Arg
         130                     135                     140

AGA GAA CAG TGT TAT GCT AGA CAT TAT TAT G TT AGG GGA GGT GTA GTA         480
Arg Glu Gln Cys Tyr Ala Arg His Tyr Tyr V al Arg Gly Gly Val Val
145                     150                     155                    160

GGT GAT GCT ATT CCT GAT GAA GCT GTG AAT C AA GAT AAA AAC TTT GTG         528
Gly Asp Ala Ile Pro Asp Glu Ala Val Asn G ln Asp Lys Asn Phe Val
                    165                     170                    175

TTA CCT GCA CAA GGC ACT CAG CAA CAA AAG G AT ATA GCT AGT TCT ATA         576
Leu Pro Ala Gln Gly Thr Gln Gln Gln Lys A sp Ile Ala Ser Ser Ile
                    180                     185                    190

TAT TTT CCA ACT GTT AGT GGT TCC TTA GTA A CT TCT GAT GCT CAA TTA         624
Tyr Phe Pro Thr Val Ser Gly Ser Leu Val T hr Ser Asp Ala Gln Leu
         195                     200                     205

TTT AAC AGA CCA TTT TGG TTA CGC AGA GCA C AA GGG CAA AAT AAC GGG         672
Phe Asn Arg Pro Phe Trp Leu Arg Arg Ala G ln Gly Gln Asn Asn Gly
         210                     215                     220

AT                                                                       674

(2) INFORMATION FOR SEQ ID NO: 9:

(i) SEQUENCE CHARACTERISTICS:
        (A) LENGTH: 686 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 684

(xi) SEQUENCE DESCRIPTION: SEQ ID NO: 9:

GGG AGA GGA CAG CCA TTA GGC GTT GGT ACC A GT GGA CAT CCA CTG TTT          48
Gly Arg Gly Gln Pro Leu Gly Val Gly Thr S er Gly His Pro Leu Phe
 1               5                      10                      15

AAC AAA GTT AAT GAT GCC GAA AAT CCC TTA G CT TAC AGG GCA CAG GCC          96
Asn Lys Val Asn Asp Ala Glu Asn Pro Leu A la Tyr Arg Ala Gln Ala
                 20                      25                     30

TTT TCT ACT GAT GAT AGG CAA AAC ACA TCC T TT GAT CCT AAA CAA ATA         144
Phe Ser Thr Asp Asp Arg Gln Asn Thr Ser P he Asp Pro Lys Gln Ile
             35                      40                     45

CAA ATG TTT ATA ATA GGT TGT GCA CCC TGT A TT GGA GAG CAT TGG GAT         192
Gln Met Phe Ile Ile Gly Cys Ala Pro Cys I le Gly Glu His Trp Asp
         50                      55                     60
```

-continued

```
GTA GGT GAA CGT TGT GCA GGA GCC AAT AAT G AA AAT GGT CGA TGC CCC      240
Val Gly Glu Arg Cys Ala Gly Ala Asn Asn G lu Asn Gly Arg Cys Pro
65              70                  75              80

CCT ATT AAA TTG GTA AAT TCA GTC ATC CAA G AT GGA GAT ATG GCA GAT      288
Pro Ile Lys Leu Val Asn Ser Val Ile Gln A sp Gly Asp Met Ala Asp
                85                  90              95

ATT GGT TAT GGA AAC CTA AAT TTC CGT ACC T TA CAG GAA AAC AGA TCT      336
Ile Gly Tyr Gly Asn Leu Asn Phe Arg Thr L eu Gln Glu Asn Arg Ser
                100                 105             110

GAT GTA AGT TTA GAT ATA GTG AAT GAA ACC T GT AAA TAT CCA GAC TTT      384
Asp Val Ser Leu Asp Ile Val Asn Glu Thr C ys Lys Tyr Pro Asp Phe
            115                 120             125

TTA AAG ATG CAG AAT GAT ATA TAT GGC GAT T CT TGC TTT TTC TTT GCT      432
Leu Lys Met Gln Asn Asp Ile Tyr Gly Asp S er Cys Phe Phe Phe Ala
        130                 135             140

CGC CGG GAG CAA TGT TAT GCA AGA CAT TTT T TT GTT CGT GGG GGT AAG      480
Arg Arg Glu Gln Cys Tyr Ala Arg His Phe P he Val Arg Gly Gly Lys
145             150                 155             160

GCG GGG GAT GAC ATT CCT GGT GCG CAA ATC G AT GCA GGT ACA TAT AAA      528
Ala Gly Asp Asp Ile Pro Gly Ala Gln Ile A sp Ala Gly Thr Tyr Lys
                165                 170             175

AAT GAT TTT TAC ATA CCT GGA GCG TCA GGT C AG ACA CAA AAG AAT ATA      576
Asn Asp Phe Tyr Ile Pro Gly Ala Ser Gly G ln Thr Gln Lys Asn Ile
                180                 185             190

GGT AAC TCG ATG TAT TTC CCA ACA GTA AGT G GC TCA TTG GTG TCT AGT      624
Gly Asn Ser Met Tyr Phe Pro Thr Val Ser G ly Ser Leu Val Ser Ser
            195                 200             205

GAT GCT CAA TTG TTT AAT AGG CCC TTC TGG C TC CAA CGG GCG CAG GGG      672
Asp Ala Gln Leu Phe Asn Arg Pro Phe Trp L eu Gln Arg Ala Gln Gly
        210                 215             220

CAA AAC AAC GGA AT                                                    686
Gln Asn Asn Gly
225
```

US 6,395,512 B1

DNA CODING FOR A PEPTIDE OF A PAPILLOMA VIRUS MAIN CAPSIDE PROTEIN AND USE THEREOF

This is a continuation of U.S. application Ser. No. 08/578,634, filed Jun. 14, 1996, now U.S. Pat. No. 6,025,163, which is the national stage application of PCT/EP95/01697, filed May 4, 1995, which claims priority to German Patent application No. P 4415743.6, filed May 4, 1994, both incorporated by reference.

TABLE OF CONTENTS

I. FIELD OF THE INVENTION
II. BACKGROUND OF THE INVENTION
III. SUMMARY OF THE INVENTION
IV. BRIEF DESCRIPTION OF THE DRAWINGS
VI. EXAMPLES
  A. Example 1: Identification of papilloma virus genome VS93-1G
  B. Example 2: Cloning of the papilloma virus genome VS93-1-G
In the claims
Abstract of the Disclosure

I. FIELD OF THE INVENTION

The present invention relates to a DNA encoding a peptide of a papilloma virus major capsid protein. Furthermore, this invention concerns a papilloma virus genome containing such a DNA. In addition, this invention relates to proteins encoded by the papilloma virus genome and to virus-like particles as well as antibodies directed thereagainst and the use thereof in diagnosis, treatment and vaccination.

II. BACKGROUND OF THE INVENTION

It is well known that papilloma viruses infect the epithelial tissue of humans and animals. Human papilloma viruses (referred to as HP viruses below) are found in benign, e.g., warts, condylomata in the genital region, and malign, e.g., carcinomas of the skin and uterus, epithelial neoplasms. Zur Hausen, 1989, *Cancer Research* 49:4677–4681. HP viruses are also considered for the development of malign tumors of the respiratory tract. Zur Hausen, 1976, *Cancer Research* 36:530. In addition, HP viruses are considered at least co-responsible for the development of squamous carcinomas of the lungs. Syrjänen, 1980, *Lung* 158:131–142.

Papilloma viruses have an icosahedral capsid without coat, which includes a circular, double-stranded DNA molecule of about 7,900 bp. The capsid comprises a major capsid protein (L1) and a minor capsid protein (L2). Both proteins, coexpressed or L1 expressed alone, result in vitro to the development of virus-like particles. Kirnbauer et al., 1993, *Journal of Virology* 67:6929–6936.

Papilloma viruses cannot be proliferated in monolayer cell culture. Therefore, their characterization is extremely difficult, the detection of papilloma viruses already creating considerable problems. This applies particularly to papilloma viruses in carcinomas of the skin. A reliable detection thereof and thus well-calculated steps thereagainst have not been possible by now.

Therefore, it is the object of the present invention to provide an agent serving for detecting papilloma viruses, particularly in carcinomas of the skin. Furthermore, an agent is to be provided which serves for taking therapeutic steps against these papilloma viruses.

According to the inventions this is achieved by the provision of the subject matters in the claims.

III. SUMMARY OF THE INVENTION

The present invention is directed to a DNA encoding a peptide of a papilloma virus major capsid protein.

The present invention is also directed to a papilloma virus genome containing such a DNA.

The present invention is further directed to proteins encoded by the papilloma virus genome and to virus-like particles as well as antibodies directed thereagainst and the use thereof in diagnosis, treatment and vaccination.

IV. BRIEF DESCRIPTION OF THE DRAWINGS

FIG. 1 shows the base sequence and the amino acid sequence, derived therefrom, of a DNA encoding a peptide of L1 of a papilloma virus. This DNA was deposited as plasmid VS93-1 with the DSM (German Collection of Microorganisms and Cell Cultures) under DSM 9133 on Apr. 12, 1994.

FIG. 2 shows the base sequence and the amino acid sequence, derived therefrom, of an DNA encoding a peptide of L1 of a papilloma virus. This DNA was deposited as plasmid CR148-59 with the DSM under DSM 9134 on Apr. 12, 1994.

FIG. 3 shows the base sequence and the amino acid sequence, derived therefrom, of an DNA encoding a peptide of L1 of a papilloma virus. This DNA was deposited as plasmid VS40-7 with the DSM under DSM 9135 on Apr. 12, 1994.

FIG. 4 shows the base sequence and the amino acid sequence, derived therefrom, of an DNA encoding a peptide of L1 of a papilloma virus. This DNA was deposited as plasmid VS20-4 with the DSM under DSM 9136 on Apr. 12, 1994.

FIG. 5 shows the base sequence and the amino acid sequence, derived therefrom, of an DNA encoding a peptide of L1 of a papilloma virus. This DNA was deposited as plasmid VS102-4 with the DSM under DSM 9137 on Apr. 12, 1994.

FIG. 6 shows the base sequence and the amino acid sequence, derived therefrom, of an DNA encoding a peptide of L1 of a papilloma virus. This DNA was deposited as plasmid VS73-1 with the DSM under DSM 9138 on Apr. 12, 1994.

FIG. 7 shows the base sequence and the amino acid sequence, derived therefrom, of an DNA encoding a peptide of L1 of a papilloma virus. This DNA was deposited as plasmid VS42-1 with the DSM under DSM 9139 on Apr. 12, 1994.

FIG. 8 shows the base sequence and the amino acid sequence, derived therefrom, of an DNA encoding a peptide of L1 of a papilloma virus. This DNA was deposited as plasmid VS92-1 with the DSM under DSM 9140 on Apr. 12, 1994.

FIG. 9 shows the base sequence and the amino acid sequence, derived therefrom, of an DNA encoding a peptide of L1 of a papilloma virus. This DNA was deposited as plasmid VS75-3 with the DSM under DSM 9141 on Apr. 12, 1994.

V. DETAILED DESCRIPTION OF THE INVENTION

Figure 10:
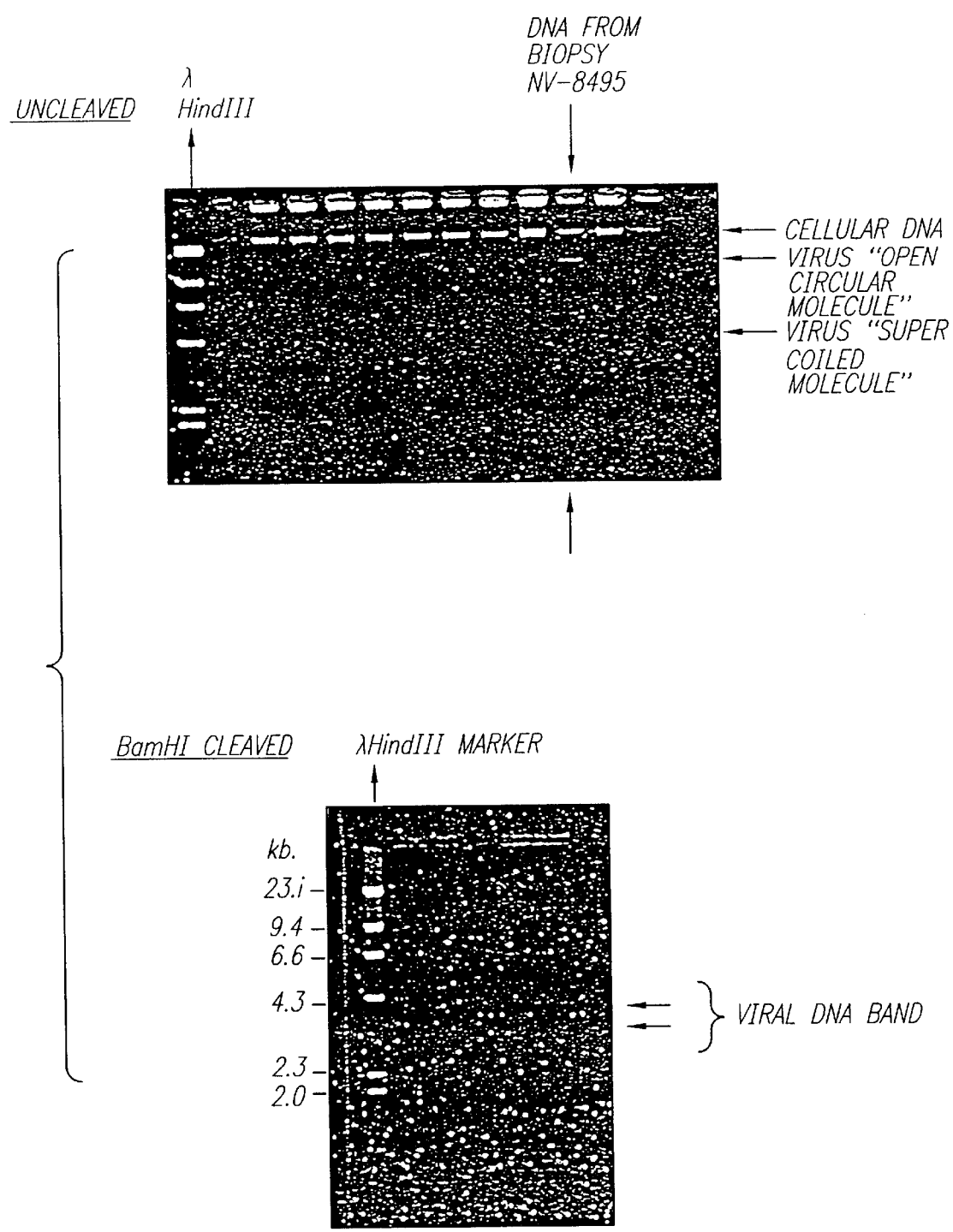

According to its objective, the subject matter of this invention relates to a DNA encoding a peptide of a papilloma virus major capsid protein (L1), the peptide comprising at least a portion of the amino acid sequence of the amino acid sequence of FIG. 1, FIG. 2, FIG. 3, FIG. 4, FIG. 5, FIG. 6, FIG. 7, FIG. 8, or FIG. 9.

The expression "at least a portion of the amino acid sequence" of the individual figures may also include a variation of one or more amino acids.

Another subject matter of the invention deals with a DNA encoding a peptide of a papilloma virus major capsid protein, the DNA comprising at least a portion of the vase sequence or the base sequence of FIG. 1, FIG. 2, FIG. 3, FIG. 4, FIG. 5, FIG. 6, FIG. 7, FIG. 8, or FIG. 9.

The expression "at least a portion of the base sequence" refers to the fact that the base sequence of the individual figures may also include a variation of one or more base pairs.

The above DNA as described in the drawings has the following sequence homology with known papilloma viruses:

| | |
|---|---|
| DNA of FIG. 1: | 82.7% with HP virus 29 |
| DNA of FIG. 2: | 75% with HP virus 49 |
| DNA of FIG. 3: | 78.5% with HP virus 49 |
| DNA of FIG. 4: | 75.6% with HP virus 25 |
| DNA of FIG. 5: | 79% with HP virus 17 |
| DNA of FIG. 6: | 73.6% with HP virus 17 |
| DNA of FIG. 7: | 73.1% with HP virus 15 |
| DNA of FIG. 8: | 82.8% with HP virus 15 |
| DNA of FIG. 9: | 75.7% with HP virus 12. |

According to the invention the above DNA may exist in a vector and an expression vector, respectively. A person skilled in the art is familiar with examples thereof. In the case of an expression vector for *E. coli*, these are e.g., pGEMEX, pUC derivatives and pGEX-2T. For the expression in yeast, e.g., pY100 and Ycpad1 have to be mentioned, while for the expression in animal cells, e.g., pKCR, pEF-BOS, cDM8 and pCEV4 have been indicated. The person skilled in the art knows suitable cells to express the above DNA present in an expression vector.

Examples of such cells comprise the *E. coli* strains HB101, DH1, X1776, JM101 and JM 109 the yeast strain *Saccharomyces cerevisiae* and the animal cells L, 3T3, FM3A, CHO, COS, Vero and Hela. The person skilled in the art knows in which way the above DNA has to be inserted in an expression vector. He is also familiar with the fact that the above DNA can be inserted in combination with a DNA encoding another protein and peptide, respectively, so that the above DNA can be expressed in the form of a fused protein.

Another subject matter of the invention relates to a papilloma virus genome which comprise the above DNA. The expression "papilloma virus genome" also comprises an incomplete genome, i.e. fragments of a papilloma virus genome, which comprise the above DNA. This may be, e.g., a DNA encoding L1 or a portion thereof.

For providing the above papilloma virus genome it is possible to use a method which comprises the following steps:

(a) isolating the total DNA from a Biopsy of epithelial neoplasm, (b) hybridizing the total DNA of (a) with the above DNA thereby detecting a papilloma virus genome included in the total DNA of (a), and (c) cloning the total DNA of (a), including the papilloma virus genome, in a vector and optionally subcloning the resulting clone, all steps originating from conventional DNA recombination technique.

As regards the isolation, hybridization and cloning of cell DNA, reference is made to Sambrook et al., Molecular Cloning, A Laboratory Manual, second edition, Cold Spring Harbor Laboratory, 1989, by way of supplement.

The expression "epithelial neoplasm" comprises any neoplasms of the epithelial tissue in humans and animals. Examples of such neoplasms are warts, condylomata in the genital region and carcinomas of the skin. The latter are used preferable here to isolate the above papilloma virus genome.

The expression "vector" comprises any vectors suitable for cloning DNA which is chromosomal and extrachromosomal, respectively. Examples of such vectors are cosmids such as pWE15 and Super Cos1, and phages such as λ-phages, e.g., λZAP expression vector, λZAPII vector and λgt10 vector. λ-phages are preferred here. The above vectors are known and obtainable from the Stratagene company.

Papilloma virus genomes according to the invention may be integrated in chromosomal DNA or present in extrachromosomal form. The person skilled in the art is familiar with methods of clarifying this. He is also familiar with methods of finding out the optimum restriction enzymes for cloning the papilloma virus genomes. He will orient himself by genomes of known papilloma viruses. In particular, the person skilled in the art will observe the above-mentioned HP viruses correspondingly.

The provision of a papilloma virus genome referred to as VS93-1-G is described by way of example. For this purposes the total DNA is isolated from a biopsy of a squamousepithelial carcinoma, cleaved by BamHI and separated electrophoretically in an agarose gel. Then, the agarose gel is subjected to a blotting method whereby the DAN is transferred to a nitrocellulose membrane. It is used in a hybridization method in which the DNA of FIG. 1 is employed, optionally in combination with a DNA of HP virus 29, as labeled sample. Hybridization with the papilloma virus DNA existing in the total DNA is obtained.

Furthermore, the above total DNA cleaved by BamHI is cloned in a λ-phage. The corresponding clones, i.e. the clones containing the papilloma virus DNA, are identified by hybridization with the DNA of FIG. 1, optionally in combination with a DNA of HP virus 29. The insert of these clones is then subjected to another cloning in a plasmid vector so as to obtain clone which contains the papilloma virus genome VS93-1-G. The genome is confirmed by sequencing.

Further papilloma virus genomes are provided in analogous manner. Corresponding to the DNAs used for their provision, they are referred to as: CR 148-59-G, VS40-7-G, VS20-4-G, VS102-4-G, VS73-1-G, VS42-1-G, VS-92-1-G and VS75-3-G, respectively.

Another subject matter of the invention relates to a protein which is encoded by the above papilloma virus genome. Such a protein is, e.g., a major capsid protein (L1) or a minor capsid protein (L2). An above protein is produced as usual. The production of L1 and L2, respectively, of the papilloma virus genome VS93-1-G is described by way of example. For this purpose, the HP virus 29 related to the DNA of FIG. 1 is used. The complete sequence thereof and the position of individual DNA regions encoding proteins are known. These DANs are identified on the papilloma virus genome VS93-1-G are parallel restriction cleavages of both genomes and subsequent hybridization with various fragments relating to the DNA encoding L1and L2, respectively. They are confirmed by sequence. The DNA encoding L1 is referred to as VS93-1-G-L1-DNA and the DNA encoding L2 is referred to as VS93-1-G-L2-DNA.

Furthermore, the DNA encoding L1 and L2, respectively, is inserted in an expression vector. Examples thereof for *E. coli*, yeast and animal cells are mentioned above. In this connection, reference it made to the vector pGEX-2T as regards the expression in *E. coli* by way of supplement. Kirnbauer et al., supra. After inserting the VS93-1-G-L1-DNA and VS93-1-g-L2-DNA, there is obtained pGEX-2T-VS93-1-G-L1 and pGEX-2T-VS93-1-G-L2, respectively. After the transformation of *E. coli*, these expression vectors express a glutathione S-transferase-L1-fused protein and glutathione S-transferase-L2-fused protein, respectively. These proteins are purified as usual.

For another expression of the above DNA encoding L1 and L2, respectively, there is mentioned the bacculovirus system and vaccinia virus system, respectively. Expression vectors usable for this purpose are, e.g., pEV mod. and pSynwtV1 for the bacculovirus system. Kirnbauer et al., supra. For the vaccinia virus system, particularly vectors including the vaccinia virus "early" (p7.5k) and "late" (Psynth, p11K) promoters are to be mention. Hagensee et al., 1993, *Journal of Virology,* 67:315–322 . The bacculovirus system is preferred here. Having inserted the above DNA encoding L1 and L2, respectively, in pEV mod., there is obtained pEVmod.-VS93-1-G-L1 and pEVmod.-VS93-1-G-L2, respectively.

The former expression vector alone or both expression vectors together lead to the formation of virus-like particles after the infection of SF-9 insect cells. In the former case, such a particle comprises an L1 protein, whereas in the latter case it contains L2 protein in addition to an L1 protein.

A virus-like particle of the latter case is also obtained in that the above SV93-1-G-L1-DNA and VS93-1-G-L2-DNA are together inserted in the expression vector pSynwtVI and the resulting pSynwtVI VS93-1-G-L1/L2 is used for infecting SF-9 insect cells. The above virus-like particles are purified as usual. They also represent a subject matter of this invention.

Another subject matter of the invention concerns an antibody directed against an above-mentioned protein and virus-like particle, respectively. Such an antibody is produced as usual. It is described by way of example for the production of an antibody which is directed against a virus-like particle comprising L1 of VS993-1-G. for this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody, for the production thereof, splenocites are taken from the mice after the above fourth injection and they are fused with myeloma cells as usual. Further cloning is also carried out according to known methods.

The present invention renders possible to detect papilloma viruses, particularly in carcinomas of the skin. For this purpose, the DNA according to the invention can be used as such or included in another DNA. The latter may also be a papilloma virus genome or a portion thereof.

Furthermore, the present invention renders possible to provide formerly unknown viruses. They are found particularly in carcinomas of the skin. In addition, this invention supplies proteins and virus-like particles which originate from these papilloma viruses. Besides, antibodies are provided which are directed against these proteins and particles, respectively.

Thus, the present invention renders possible to take diagnostic and therapeutic steps in the case of papilloma virus diseases. Moreover, it furnishes the possibility of preparing a vaccine against papilloma virus infections. Therefore, the present invention represents a break-through in the field of papilloma virus research.

The invention is explained by the examples. The following preparations and examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Identification of Papilloma Virus Genome VS93-1G

The total DNA is isolated from the biopsy WV-8495 of a squamous-epithelial carcinoma of an immunosuppressed person. 10 µg of this DNA are cleaved by the restriction enzyme BamHI and separated electrophoretically in a 0.5% agarose gel. At the same time, 10 µg of the above DNA which has not been cleaved are also separated. The result of the electrophoresis is shown in FIG. 10. It follows therefrom that a DNA molecule exists in the non-cleaved DNA in a form typical of an extrachromosomal DNA, i.e. a "super-coiled molecule" and "open circular molecule", respectively. This DNA molecule is cleaved by BamHI into two fragments.

The above agarose gel is subjected to a blotting method whereby the DNA is transferred from the agarose gel to a nitrocellulose membrane. It is used in a hybridization method in which the above DNA of FIG. 1 is employed in combination with the HP virus 29 DNA as $p^{32}$-labeled sample. Hybridization with the above DNA molecule is obtained.

The person skilled in the field of the DNA recombination technique is familiar with the above methods. Reference is made to Sambrook et al., supra, by way of supplement.

B. Example 2

Cloning of the Papilloma Virus Genome VS93-1-G

The DNA, obtained from Example 1, of biopsy WV-8495 is cleaved by the restriction enzyme BamHI. The resulting fragments are inserted in a ligase reaction in which the BamHI-cleaved and dephosphorylated vector ZAP Express is present.

The resulting recombinant DNA molecules are packaged in bacteriophages which are used for infecting bacteria. The ZAP expression vector kit offered by the Stratagene company is used for these steps. The resulting phageplaques are then subjected to a hybridization method in which the $p^{32}$-labeled DNA of FIG. 1, used in Example 1, is employed in combination with the $p^{32}$-labled HP virus 29 DNA. Hybridization with corresponding phageplaques is obtained. The two BamHI fragments of VS93-1-G are isolated therefrom and inserted in another ligase reaction together with a BamHI-cleaved, dephosphorylated plasmid vector, i.e. pBluescript. The resulting recombinant DNA molecules are used for the transformation of bacteria, i.e. *E. coli.* XI1-Blue. A bacterial clone containing the papilloma virus genome VS93-1-G is identified by restriction cleavages and hybridization with the above DNA samples, respectively. The plasmid of this bacterial clone is referred to as pBlue-VS93-1-G.

All references cited within the body of the instant specification are hereby incorporated by reference in their entirety.

What is claimed is:

1. An isolated polynucleotide consisting essentially of:
   (a) the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9;
   (b) a nucleotide sequence hybridizing to the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; or
   (c) the complement of (a) or (b);
   wherein the polynucleotide has a homology of at least 90% to the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

2. An isolated polynucleotide encoding a peptide of a papilloma virus major capsid protein, wherein the said polynucleotide has been obtained using the following steps:
   (a) incubating total DNA isolated from a biopsy of epithelial neoplasm with a nucleic acid having at least a portion of the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, under a condition that allows hybridization of a polynucleotide included in the total DNA to said nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; and
   (b) identifying and isolating a polynucleotide that hybridizes to the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9 in step (a);
   wherein the polynucleotide has a homology of at least 90% to the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

3. An isolated polynucleotide, consisting essentially of (a) a nucleic acid encoding the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or (b) the complement of (a).

4. An isolated polynucleotide, wherein the polynucleotide consists essentially of the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or the complement thereof.

5. An expression vector comprising the polynucleotide of claim 1 or 2.

6. An expression vector comprising the polynucleotide of claim 3.

7. A host cell comprising the expression vector of claim 5.

8. A host cell comprising the expression vector of claim 6.

9. A method of producing a peptide of a papilloma virus major capsid protein, comprising cultivating the host cell of claim 7 under suitable conditions.

10. A method of producing a peptide of a papilloma virus major capsid protein, comprising cultivating the host cell of claim 8 under suitable conditions.

11. A method of detecting a papilloma virus DNA, comprising:
  (a) hybridizing under stringent conditions at least a portion of the polynucleotide of claim 1, 2, 3, or 4 to a DNA sample; and
  (b) identifying virus in said DNA sample by detecting a hybridization signal.

12. A composition comprising the polynucleotide of claim 1, 2, 3, or 4 as reagent for diagnosis and a diagnostically acceptable carrier.

13. A plasmid comprising the polynucleotide of claim 1 or 2.

14. A plasmid comprising the polynucleotide of claim 3.

15. A host cell comprising the plasmid of claim 13.

16. A host cell comprising the plasmid of claim 14.

* * * * *